US008648202B2

(12) United States Patent
Hoge et al.

(10) Patent No.: US 8,648,202 B2
(45) Date of Patent: Feb. 11, 2014

(54) BIS(PERFLUOROALKYL)PHOSPHINOUS ACIDS AND DERIVATIVES AND USE THEREOF

(75) Inventors: Berthold Hoge, Bielefeld (DE); Anne Julia Bader, Bielefeld (DE); Boris Kurscheid, Cologne (DE); Nikolai (Mykola) Ignatyev, Duisburg (DE); Emil Ferdinand Aust, Mainz (DE)

(73) Assignee: Merck Patent GmbH, Darmstadt (DE)

( * ) Notice: Subject to any disclaimer, the term of this patent is extended or adjusted under 35 U.S.C. 154(b) by 166 days.

(21) Appl. No.: 13/055,561

(22) PCT Filed: Jul. 10, 2009

(86) PCT No.: PCT/EP2009/005025
§ 371 (c)(1),
(2), (4) Date: Jan. 24, 2011

(87) PCT Pub. No.: WO2010/009818
PCT Pub. Date: Jan. 28, 2010

(65) Prior Publication Data
US 2011/0124873 A1 May 26, 2011

(30) Foreign Application Priority Data

Jul. 25, 2008 (EP) .................................... 08013426

(51) Int. Cl.
*C07F 9/46* (2006.01)
*C07F 9/52* (2006.01)
*C07F 15/00* (2006.01)

(52) U.S. Cl.
USPC ................. 546/304; 568/14; 568/16; 556/20; 556/405; 546/347; 546/344; 548/560; 548/562; 564/291; 564/296

(58) Field of Classification Search
None
See application file for complete search history.

(56) References Cited

FOREIGN PATENT DOCUMENTS

DE 21 10 767 A1 9/1972
WO WO 03/087113 A1 3/2003

OTHER PUBLICATIONS

Badoiu et al. Chem. Asian J., 2008, 3, 1298-1311. Published online Jul. 16, 2008.*
Hoge et al. Chem. Eur. J. 2006, 12, 9019-9024.*
Khokhryakov et al. Zhurnal Obshchei Khimii, 55 (11), 2622, 1985, and Abstract cited from SciFinder.*
International Search Report of PCT/EP2009/005025, Date of Completion Oct. 9, 2009, Date of Mailing Oct. 27, 2009.
Codell, M. :"Hydrolosis of heptafluoropropylphosphonous diiodide and bishepetafluoropropylohosphinous iodide Formation of bishpetafluoropropylphospine," Journal of Cheimical and Enginieering Data, Bd. 8, Nr. 3, 1963m, Seite 460, XP002546060 Bis-heptafluoropropyl-dimethylamino-phosphin.
Emelus, Smith: The Heptafluorpropyl—phosphin, Derivates, Journal of the Chemical Society, 1959, Seiten 375-381, XP002546061.
Ang. H. et al: "Cyclic Phosphines and Arsines," Australian Journal of Chemistry, Bd. 25, 1972, Seiten 493-498, XP009122722 Iodobis (pentafluoroehyl) phosphin, Chlorobis (pentafluoroethyl) phosphin.
Inorganic Chemistry, "The Inorganic Chemistry of Carbon Difluoride," W.Mahler p. 230.
Inorganic Chemistry, D.D. Magnelli et al. "Perfluorophenylphosphine Derivatives", 1966, vol. 5, pp. 457-461.
Zh. Obsh. Khim, (Russ.), 54 (1984), 2, pp. 334-339, L.M.
J. Chem. Daelton Trans, Transition Metal Carbon-Bonds. Part XLII. Complexes of Nickel, Palladium, Platinum, Rhodium and Iridum with the Tridentate Ligand 2,6 Bis[(di-t-butylphosphino) methyl] phenyl.
Chem Rev. 2003, 103, pp. 1759-1792, M.E. van der Boom et al., Cyclometalated Phosphine-Based Pincer Complexes: Mechanistic Insight in Catalysis, Coordination and Bond Activation.
GIT Labor-Fachzeitschrift, Nr. 4, 2008, pp. 400-403, J Krämer et al.
Inorganic Chemistry, E. Redel et al., fFirst Correlation of Nanoparticle Size-Dependent Formation with the Ionic Anion Molecular Volume, 47, 2008, pp. 14-16.
Angew. Chem. Int. Ed. 2008, 47, pp. 6814-6816, B. Hoge et al. "Tetrakis[2,4-bis(trifluoromethyl)phenyl]diphosphoxane: An Anhydride of a Phosphinous Acid".

* cited by examiner

*Primary Examiner* — Yun Qian
(74) *Attorney, Agent, or Firm* — Millen, White, Zelano & Branigan, P.C.

(57) ABSTRACT

The invention relates to bis(perfluoroalkyl)phosphinous acids, bis(perfluoroalkyl)thiophosphinous acids and derivatives, the synthesis thereof and the use thereof, in particular for the synthesis of air-stable metal complexes for catalytic processes.

17 Claims, No Drawings

BIS(PERFLUOROALKYL)PHOSPHINOUS ACIDS AND DERIVATIVES AND USE THEREOF

The invention relates to bis(perfluoroalkyl)phosphinous acids or bis(perfluoroalkyl)thiophosphinous acids, derivatives thereof, the synthesis thereof and the use thereof, in particular for the synthesis of air-stable metal complexes for catalytic processes.

Phosphinous acids are of great interest for the synthesis of air-stable metal complexes for homogeneous catalysis. Palladium complexes with bis(tertbutyl)phosphinous acid are known which have high activity for cross-coupling reactions which result in the formation of new C—C, C—N or C—S bonds.

The phosphinous acids known to date containing alkyl or aryl groups are very unstable compounds and cannot be isolated. Stabilisation is generally carried out by complexing with a transition metal. Such transition-metal complexes are marketed, for example, by the company COMBIPHOS CATALYSIS Inc., Princeton, N.J., USA.

The object of the invention was to prepare stable phosphinous acids which are suitable for the preparation of transition-metal complexes for homogeneous synthesis.

Surprisingly, it has been found that phosphinous acids can be stabilised in the acid form by the introduction of perfluoroalkyl groups having from two C atoms on the phosphorus atom. Although the known bis(trifluoromethyl)phosphinous acid $(CF_3)_2POH$ can be isolated, it has, however, low stability, is pyrophoric in air and the complex synthesis thereof prevents practical application of this acid. The low stability is probably caused by possible elimination of difluorocarbene, a process which is known in the literature for trifluoromethylated phosphorus compounds, for example in W. Mahler, Inorg. Chem. 2 (1963), 230.

By contrast, bis(pentafluorophenyl)phosphinous acid, as incorrectly described in D. D. Magnelli, G. Tesi, j. U. Lowe, W. E. McQuistion, Inorg. Chem. 1966, 5, 457-461, exists in the solid state, but also in solutions of chloroform, toluene or diethyl ether exclusively in the phosphine oxide form $(C_6F_5)_2P(O)H$ and not in the form of the phosphinous acid $(C_6F_5)_2POH$.

The phosphinous acids of the formula I, as explained below, can be synthesised starting from industrially accessible materials, in contrast to the known bis(trifluoromethyl)phosphinous acid. In addition, it has been found, surprisingly, that salts of the phosphinous acid according to the invention have excellent properties and can be used, in particular, as ionic liquids.

The thiophosphinous acids of the formula I, as explained below, can be prepared from the phosphinous acid chlorides.

Ionic liquids or liquid salts are ionic species which consist of an organic cation and a generally inorganic or organic anion. They do not contain any neutral molecules and usually have melting points below 373 K.

The properties of ionic liquids, for example melting point, thermal and electrochemical stability, viscosity, are strongly influenced by the nature of the anion. By contrast, the polarity and hydrophilicity or lipophilicity can be varied through a suitable choice of the cation/anion pair.

The invention therefore relates to compounds of the formula I

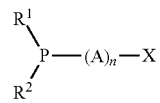

or corresponding salts of the formula II

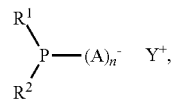

where
$R^1$ and $R^2$ each stand, independently of one another, for straight-chain or branched perfluoroalkyl groups having 2 to 12 C atoms,
A stands for O or S,
X stands for H, straight-chain or branched alkyl groups having 1 to 18 C atoms, cycloalkyl having 3 to 7 C atoms, alkenyl having 2 to 12 C atoms, alkynyl having 2 to 12 C atoms, aryl, alkyl-aryl, $Si(R^0)_3$ or $Sn(R^0)_3$ if n stands for the integer 1,
X stands for H, halogen, $N(R^0)_2$ if n stands for the integer 0,
$Y^+$ stands for ammonium, phosphonium, tritylium, guanidinium, heterocyclic cations containing at least one nitrogen or phosphorus atom, $Ag^+$, $Li^+$, $Na^+$, $K^+$, $Rb^+$ or $Cs^+$ if n stands for the integer 1, and
$R^0$ stands for a straight-chain or branched alkyl group having 1 to 8 C atoms.
$R^1$ and $R^2$ may be different or identical. $R^1$ and $R^2$ are particularly preferably identical.

A preferably stands for O.

Straight-chain or branched perfluoroalkyl groups having 2 to 12 C atoms conform to the formula $C_mF_{2m+1}$, where m=2, 3, 4, 5, 6, 7, 8, 9, 10, 11 or 12. $R^1$ and $R^2$ preferably each stand, independently of one another, for pentafluoroethyl, heptafluoropropyl or linear or branched nonafluorobutyl or perfluorohexyl. $R^1$ and $R^2$ very particularly preferably stand for pentafluoroethyl or linear nonafluorobutyl.

Straight-chain or branched alkyl groups having 1 to 4, 1 to 6, 1 to 8, 1 to 12, 1 to 18 or 1 to 20 C atoms conform to the formula $C_pH_{2p+1}$, where p=1, 2, 3 or 4, or 1, 2, 3, 4, 5 or 6, or 1, 2, 3, 4, 5, 6, 7 or 8, or 1, 2, 3, 4, 5, 6, 7, 8, 9, 10, 11 or 12, or 1, 2, 3, 4, 5, 6, 7, 8, 9, 10, 11, 12, 13, 14, 15, 16, 17 or 18, or 1, 2, 3, 4, 5, 6, 7, 8, 9, 10, 11, 12, 13, 14, 15, 16, 17, 18, 19 or 20, for example methyl, ethyl, isopropyl, propyl, butyl, i-butyl or tert-butyl, furthermore also pentyl, 1-, 2- or 3-methylbutyl, 1,1-, 1,2- or 2,2-dimethylpropyl, 1-ethylpropyl or hexyl, furthermore also heptyl, octyl, furthermore also nonyl, decyl, undecyl, dodecyl, tridecyl, tetradecyl, pentadecyl, hexadecyl, heptadecyl or octadecyl, furthermore also nonadecyl or eicosyl.

A straight-chain or branched alkenyl, preferably having 2 to 10 C atoms, is, for example, allyl, 2- or 3-butenyl, isobutenyl, sec-butenyl, furthermore 4-pentenyl, isopentenyl, hexenyl, octenyl or decenyl.

A straight-chain or branched alkynyl, preferably having 3 to 10 C atoms, is, for example, propargyl, 2- or 3-butynyl, furthermore 4-pentynyl, hexynyl, octynyl or decynyl.

Cycloalkyl having 3 to 7 C atoms denotes unsubstituted saturated or partially unsaturated cycloalkyl groups having 3-7 C atoms, for example cyclopropyl, cyclobutyl, cyclopentyl, cyclohexyl, cycloheptyl, cyclopentenyl, cyclohexenyl or cycloheptenyl, each of which may be substituted by $C_1$- to $C_6$-alkyl groups.

Aryl stands, for example, for substituted or unsubstituted phenyl, naphthyl or anthryl. Aryl particularly preferably stands for unsubstituted or substituted phenyl.

Substituted phenyl denotes phenyl which is substituted by $C_1$- to $C_6$-alkyl, $C_2$- to $C_6$-alkenyl, $NO_2$, CN, F, Cl, Br, I, OH, unfluorinated, partially fluorinated or perfluorinated $C_1$-$C_6$-alkoxy, $SCF_3$, $SO_2CF_3$, COOH, C(O)OR", C(O)X', C(O)NR"$_2$, C(O)H, C(O)R", $SO_2$X', $SO_2$NR"$_2$ or $SO_3$H, where X' denotes F, Cl or Br and R" denotes an unfluorinated, partially fluorinated or perfluorinated $C_1$- to $C_6$-alkyl or $C_3$- to $C_7$-cycloalkyl as defined, for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl. Aryl is very particularly preferably unsubstituted phenyl.

Unfluorinated $C_1$-$C_6$-alkoxy corresponds to an alkoxy group of the formula $OC_pH_{2p+1}$, where p=1, 2, 3, 4, 5 or 6, for example methoxy, ethoxy, propoxy, butoxy, pentoxy or hexoxy, where the alkyl groups of the alkoxy groups may be straight-chain or branched. In the case of perfluorinated alkoxy groups, all H atoms of the above-mentioned formula have been correspondingly replaced by F. In the case of alkoxy groups which are partially substituted by F, only some H have been replaced by F.

Alkyl-aryl denotes, for example, benzyl, phenylethyl, phenylpropyl, phenylbutyl, phenylpentyl or phenylhexyl, particularly preferably benzyl.

$R^0$ stands for a straight-chain or branched alkyl group having 1 to 8 C atoms, for example methyl, ethyl, propyl, n-butyl, s-butyl, tert-butyl, hexyl or octyl, particularly preferably for methyl or butyl.

Halogen denotes Cl, Br or I, preferably Cl or Br.

In formula I, X preferably stands for H if n=1, i.e. for a bis(perfluoroalkyl)phosphinous acid if A=O or for a bis(perfluoroalkyl)thiophosphinous acid if A=S.

Derivatives of this phosphinous acid are preferably compounds of the formula I in which X preferably stands for a straight-chain or branched alkyl group having 1 to 4 C atoms, phenyl, benzyl, trimethylsilyl or tributylstannyl if n=1.

For A=S, preference is given to compounds of the formula I in which X stands for H and n=1.

In formula I, X preferably stands for H or halogen if n=0. This applies to compounds of the formula I where A=O or S, in particular to compounds of the formula I where A=O.

In formula II, $Y^+$ stands either for a metallic cation, for example $Ag^+$, $Li^+$, $Na^+$, $K^+$, $Rb^+$ or $Cs^+$, or for an organic cation from the group ammonium, phosphonium, tritylium, guanidinium or a heterocyclic cation containing at least one nitrogen or phosphorus atom if n=1.

In the case of the metallic cations, $Y^+$ preferably stands for $Ag^+$, $Li^+$, $Na^+$ or $K^+$, particularly preferably Li+ Lithium salts are particularly interesting salts for electrochemical applications, for example as conductive salts in electrochemical cells.

The compounds of the formula II with the organic cations from the group ammonium, phosphonium, tritylium, guanidinium or a heterocyclic cation containing at least one nitrogen or phosphorus atom if n=1 are used, in particular, as ionic liquids.

Preferred for ammonium are ammonium cations of the formula (1)

$$[NR_4]^+ \quad (1),$$

where
R in each case, independently of one another, can be
H, OR', NR'$_2$, with the proviso that a maximum of one substituent R in formula (1) is OR', NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by alkyl groups having 1-6 C atoms,
phenyl, which may be substituted by alkyl groups having 1-6 C atoms, where one or more R may be partially or fully substituted by halogens, in particular —F and/or —Cl, or partially by —OH, —OR', —CN, —C(O)OH, —C(O)NR'$_2$, —SO$_2$NR'$_2$, —C(O)X', —SO$_2$OH, —SO$_2$X', —NO$_2$, and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R' can be =H, unfluorinated, partially fluorinated or perfluorinated $C_1$- to $C_6$-alkyl, $C_3$- to $C_7$-cycloalkylu, which may be substituted by alkyl groups having 1-6 C atoms, unsubstituted or substituted phenyl and X' can be =halogen.

Preferred for phosphonium are phosphonium cations of the formula (2)

$$[PR^3_4]^+ \quad (2),$$

where
$R^3$ in each case, independently of one another, can be
H, OR', NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by alkyl groups having 1-6 C atoms,
phenyl, which may be substituted by alkyl groups having 1-6 C atoms, where one or more $R^3$ may be partially or fully substituted by halogens, in particular —F and/or —Cl, or partially by —OH, —OR', —CN, —C(O)OH, —C(O)NR'$_2$, —SO$_2$NR'$_2$, —C(O)X', —SO$_2$OH, —SO$_2$X', —NO$_2$, and where one or two non-adjacent carbon atoms in $R^3$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R' can be =H, unfluorinated, partially fluorinated or perfluorinated $C_1$- to $C_6$-alkyl, $C_3$- to $C_7$-cycloalkyl, which may be substituted by alkyl groups having 1-6 C atoms, unsubstituted or substituted phenyl and X' can be =halogen.

Preferred for guanidinium are guanidinium cations of the formula (3)

$$[C(NR^8R^9)(NR^{13}R^{11})(NR^{12}R^{13})]^+ \quad (3),$$

where
$R^8$ to $R^{13}$ each, independently of one another, denote
H, —CN, NR'$_2$, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by alkyl groups having 1-6 C atoms,
phenyl, which may be substituted by alkyl groups having 1-6 C atoms, where one or more of the substituents $R^8$ to $R^{13}$ may be partially or fully substituted by halogens, in particular —F and/or —Cl, or partially by —OH, —OR', —CN, —C(O)OH, —C(O)NR'$_2$, —SO$_2$NR'$_2$, —C(O)X', —SO$_2$OH, —SO$_2$X', —NO$_2$ and where one or two non-adjacent carbon atoms in $R^8$ to $R^{13}$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, unfluorinated, partially fluorinated or perfluorinated C$_1$- to C$_6$-alkyl, C$_3$- to C$_7$-cycloalkyl, which may be substituted by alkyl groups having 1-6 C atoms, unsubstituted or substituted phenyl and X'=halogen.

Preferred for a heterocyclic cation containing at least one nitrogen atom are heterocyclic cations of the formula (4)

$$[HetN]^+ \quad (4),$$

where
HetN$^+$ denotes a heterocyclic cation selected from the group

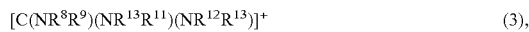

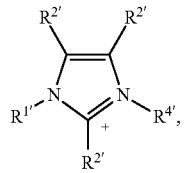
imidazolium

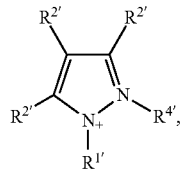
1H-pyrazolium

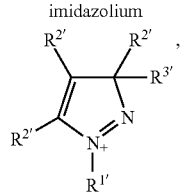
3H-pyrazolium   4H-pyrazolium

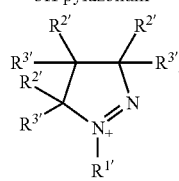
1-pyrazolinium   2-pyrazolinium

-continued

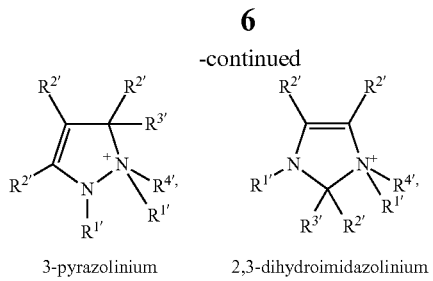
3-pyrazolinium   2,3-dihydroimidazolinium

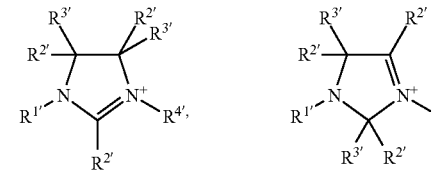
4,5-dihydroimidazolinium   2,5-dihydroimidazolinium

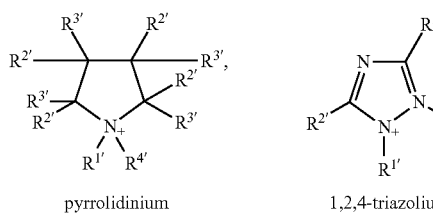
pyrrolidinium   1,2,4-triazolium

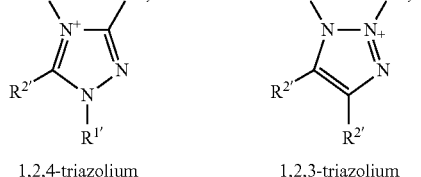
1,2,4-triazolium   1,2,3-triazolium

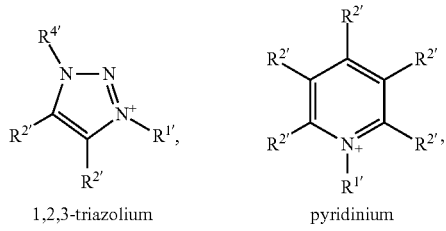
1,2,3-triazolium   pyridinium

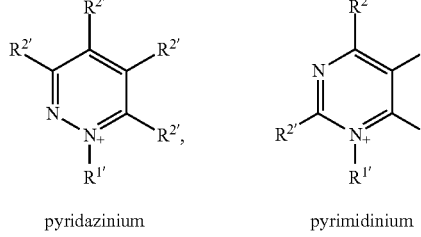
pyridazinium   pyrimidinium

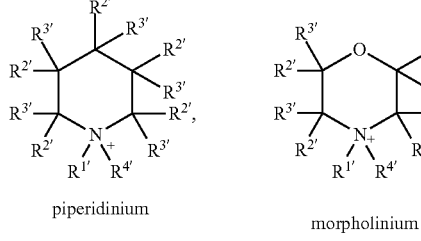
piperidinium   morpholinium

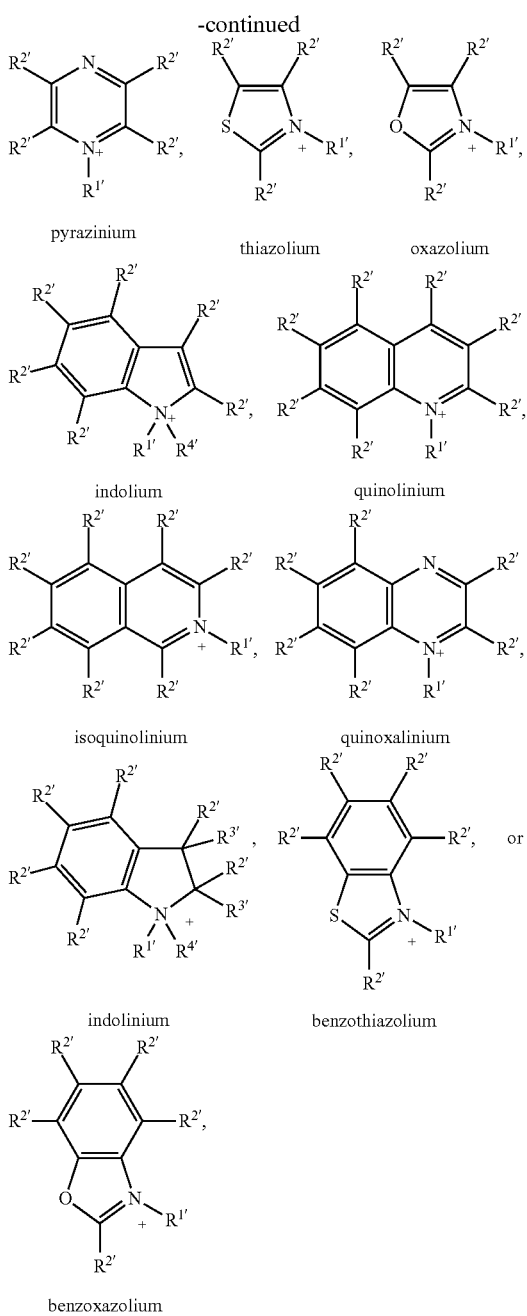

pyrazinium
thiazolium
oxazolium indolium
quinolinium isoquinolinium
quinoxalinium or indolinium
benzothiazolium benzoxazolium where the substituents
$R^{1'}$ to $R^{4'}$ each, independently of one another, denote
H, —CN, —OR', —NR'$_2$, —P(O)R'$_2$, —P(O)(OR')$_2$, —P(O)(NR'$_2$)$_2$, —C(O)R', —C(O)OR',
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by alkyl groups having 1-6 C atoms,
phenyl, which may be substituted by alkyl groups having 1-6 C atoms, saturated, partially or fully unsaturated heteroaryl, heteroaryl-$C_1$-$C_6$-alkyl or aryl-$C_1$-$C_6$-alkyl, where the substituents $R^{1'}$, $R^{2'}$, $R^{3'}$ and/or $R^{4'}$ together may also form a ring system,
where one or more substituents $R^{1'}$ to $R^{4'}$ may be partially or fully substituted by halogens, in particular —F and/or —Cl, or —OH, —OR', —CN, —C(O)OH, —C(O)NR'$_2$, —SO$_2$NR'$_2$, —C(O)X', —SO$_2$OH, —SO$_2$X', —NO$_2$, but where $R^{1'}$ and $R^{4'}$ cannot simultaneously be fully substituted by halogens, and where, in the substituents $R^{1'}$ to $R^{4'}$, one or two non-adjacent carbon atoms which are not bonded to the heteroatom may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, unfluorinated, partially fluorinated or perfluorinated $C_1$- to $C_6$-alkyl, $C_3$- to $C_7$-cycloalkyl, which may be substituted by alkyl groups having 1-6 C atoms, unsubstituted or substituted phenyl and X'=halogen.

Preference is given for a heterocyclic cation containing at least one phosphorus atom to heterocyclic cations of the formula (5)

[HetP]$^+$     (5), where
HetP$^+$ denotes a heterocyclic cation selected from the group

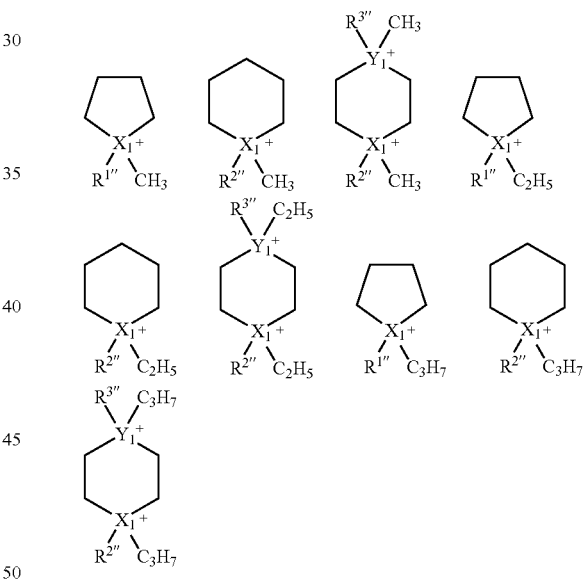

where
$X_1$ stands for P,
$Y_1$ stands for N or P,
$R^{1''}$, $R^{2''}$ and $R^{3''}$ each, independently of one another, have the meaning H, straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by alkyl groups having 1-6 C atoms,
phenyl, which may be substituted by alkyl groups having 1-6 C atoms, saturated, partially or fully unsaturated heteroaryl, heteroaryl-$C_1$-$C_6$-alkyl or aryl-$C_1$-$C_6$-alkyl, and where one or more substituents $R^{1''}$ to $R^{3''}$ may be partially or fully substituted by halogens, in particular —F and/or —Cl.

Fully unsaturated substituents in the sense of the present invention are also taken to mean aromatic substituents.

The substituents R of the compounds of the formula (1) are preferably H, straight-chain or branched alkyl groups having 1 to 20 C atoms, in particular $C_1$- to $C_6$-alkyl groups, saturated or partially unsaturated $C_3$- to $C_7$-cycloalkyl groups, which may be substituted by $C_1$- to $C_6$-alkyl groups, or phenyl, which may be substituted by $C_1$- to $C_6$-alkyl groups, in particular unsubstituted phenyl. R very particularly preferably stands for straight-chain or branched alkyl groups having 1 to 4 C atoms.

The substituents R in formula (1) may be identical or different. Particular preference is given to compounds in which three substituents R are identical and one substituent R is different or in which all four substituents are identical. Very particularly preferably, three substituents R are identical and one substituent R is different.

The substituents $R^3$ of the compounds of the formula (2) are preferably H, straight-chain or branched alkyl groups having 1 to 20 C atoms, in particular $C_1$- to $C_8$-alkyl groups, saturated or partially unsaturated $C_3$- to $C_7$-cycloalkyl groups, which may be substituted by $C_1$- to $C_8$-alkyl groups, in particular cyclohexyl, or phenyl, which may be substituted by $C_1$- to $C_8$-alkyl groups, in particular unsubstituted phenyl. $R^3$ very particularly preferably stands for straight-chain or branched alkyl groups having 1 to 4 C atoms. The substituents $R^3$ in formula (1) may be identical or different. Particular preference is given to compounds in which three substituents $R^3$ are identical and one substituent $R^3$ is different or in which all four substituents are identical. Very particularly preferably, three substituents $R^3$ are identical and one substituent $R^3$ is different.

The substituents R and $R^3$ are particularly preferably each, independently of one another, methyl, ethyl, isopropyl, propyl, butyl, i-butyl, tert-butyl, pentyl, hexyl, octyl, decyl or tetradecyl.

The substituents $R^8$ to $R^{13}$ of the compounds of the formula (3) are preferably each, independently of one another, H, straight-chain or branched alkyl groups having 1 to 20 C atoms, in particular $C_1$- to $C_4$-alkyl groups, and saturated or unsaturated, i.e. also aromatic, $C_3$- to $C_7$-cycloalkyl groups, which may be substituted by $C_1$- to $C_6$-alkyl groups, in particular phenyl.

Up to four substituents of the guanidinium cation of the formula (3) may also be bonded in pairs in such a way that mono-, bi- or polycyclic cations are formed.

Without restricting generality, examples of such guanidinium cations are:

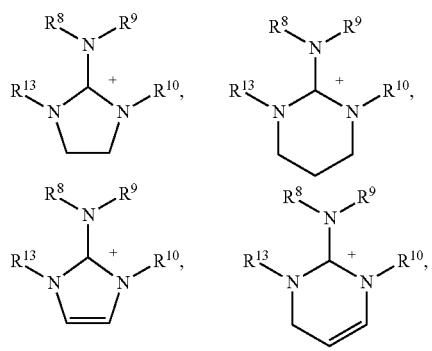
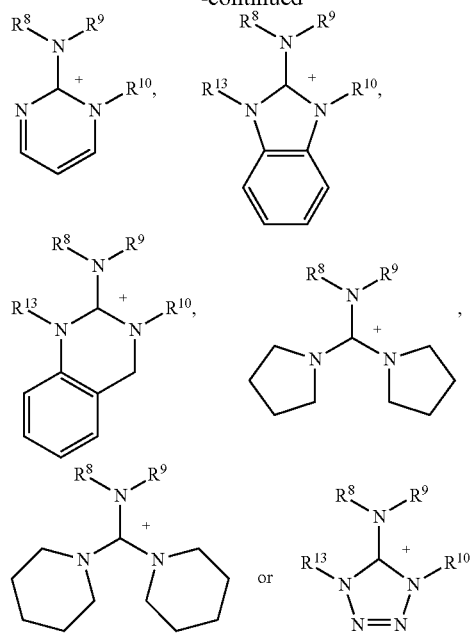

where the substituents $R^8$ to $R^{10}$ and $R^{13}$ can have a meaning or particularly preferred meaning indicated above.

If desired, the carbocycles or heterocycles of the guanidinium cations indicated above may also be substituted by $C_1$- to $C_6$-alkyl, $C_1$- to $C_6$-alkenyl, $NO_2$, CN, F, Cl, Br, I, OH, $C_1$-$C_6$-alkoxy, $SCF_3$, $SO_2CF_3$, C(O)OH, C(O)OR', $SO_2NR'_2$, $SO_2X'$ or $SO_3H$, where X and R' have a meaning indicated above, substituted or unsubstituted phenyl or an unsubstituted or substituted heterocycle.

The substituents $R^8$ and $R^9$, $R^{10}$ and $R^{11}$ and $R^{12}$ and $R^{13}$ in compounds of the formulae for guanidinium cations as described above may be identical or different. $R^8$ to $R^{13}$ are particularly preferably each, independently of one another, methyl, ethyl, n-propyl, isopropyl, n-butyl, tert-butyl, i-butyl, phenyl or cyclohexyl, very particularly preferably methyl, ethyl, n-propyl, isopropyl or n-butyl.

In accordance with the invention, suitable substituents $R^{1'}$ to $R^{4'}$ of compounds of the formula (4), besides H, are preferably: $C_1$- to $C_{20}$-, in particular $C_1$- to $C_{12}$-alkyl groups, and saturated or partially unsaturated $C_3$- to $C_7$-cycloalkyl groups, which may be substituted by $C_1$- to $C_6$-alkyl groups, preferably cyclohexyl, or phenyl, which may be substituted by $C_1$- to $C_6$-alkyl groups.

The substituents $R^{1'}$ and $R^{4'}$ are each, independently of one another, particularly preferably methyl, ethyl, isopropyl, propyl, butyl, i-butyl, tert-butyl, pentyl, hexyl, octyl, decyl, cyclohexyl, phenyl or benzyl. They are very particularly preferably methyl, ethyl, n-butyl or n-hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular H, methyl, ethyl, isopropyl, propyl, butyl, i-butyl, tert-butyl, cyclohexyl, phenyl or benzyl. $R^{2'}$ is particularly preferably H, methyl, ethyl, isopropyl, propyl, butyl or i-butyl. $R^{2'}$ and $R^{3'}$ are very particularly preferably H.

In accordance with the invention, suitable substituents $R^{1''}$ to $R^{3''}$ of compounds of the formula (5), besides H, are preferably: $C_1$- to $C_{20}$, in particular $C_1$- to $C_{12}$-alkyl groups, and saturated or partially unsaturated $C_3$- to $C_7$-cycloalkyl groups, which may be substituted by $C_1$- to $C_6$-alkyl groups, or phenyl, which may be substituted by $C_1$- to $C_6$-alkyl groups.

$R^{1''}$ is particularly preferably methyl, ethyl, isopropyl, n-propyl, n-butyl or i-butyl.

$R^{2''}$ is particularly preferably methyl, ethyl, isopropyl, n-propyl, n-butyl or i-butyl.

$R^{3''}$ is particularly preferably methyl, ethyl, isopropyl, n-propyl, n-butyl or i-butyl.

A straight-chain or branched alkenyl having 2 to 20 C atoms, in which a plurality of double bonds may also be present, is, for example, ethenyl, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{16}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$. R' and X have the meanings indicated above.

Unsubstituted saturated or partially unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups.

In the substituents R, R$^3$, R$^8$ to R$^{13}$ or R$^{1'}$ to R$^{4'}$, one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—, where R'=unfluorinated, partially fluorinated or perfluorinated $C_1$- to $C_6$-alkyl, $C_3$- to $C_7$-cycloalkyl, which may be substituted by $C_1$- to $C_6$-alkyl groups, unsubstituted or substituted phenyl.

Without restricting generality, examples of substituents R, R$^3$, R$^8$ to R$^{13}$ and R$^{1'}$ to R$^{4'}$ modified in this way are:
—OCH$_3$, —OC H(CH$_3$)$_2$, —CH$_2$OC H$_3$, —CH$_2$—CH$_2$—O—CH$_3$, —C$_2$H$_4$OCH(CH$_3$)$_2$, —C$_2$H$_4$C$_2$H$_5$, —C$_2$H$_4$SCH (CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—C$_4$H$_9$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_6$)C$_2$F$_6$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$, —C(O)C$_6$H$_5$ or P(O)(C$_2$H$_5$)$_2$.

In R', $C_3$- to $C_7$-cycloalkyl is, for example, preferably cyclopropyl, cyclobutyl, cyclopentyl, cyclohexyl or cycloheptyl.

In R', substituted phenyl denotes phenyl which is substituted by unfluorinated, partially fluorinated or perfluorinated $C_1$- to $C_6$-alkyl, $C_2$- to $C_6$-alkenyl, NO$_2$, CN, F, Cl, Br, I, OH, unfluorinated, partially fluorinated or perfluorinated $C_1$-$C_6$-alkoxy, SCF$_3$, SO$_2$CF$_3$, COOH, SO$_2$X', SO$_2$NR''$_2$ or SO$_3$H, where X' denotes F, Cl or Br and R'' denotes a unfluorinated, partially fluorinated or perfluorinated $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In R$^{1'}$ to R$^{4'}$ or R$^{1''}$ to R$^{3''}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, NO$_2$, CN, F, Cl, Br, I, OH, $C_1$-$C_6$-alkoxy, SCF$_3$, SO$_2$CF$_3$, COOH, SO$_2$X', SO$_2$NR''$_2$ or SO$_3$H, where X' and R'' have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyridinylpentyl, pyridinylhexyl, where the heterocycles described above may furthermore be linked to the alkylene chain in this way.

HetN$^+$ is preferably

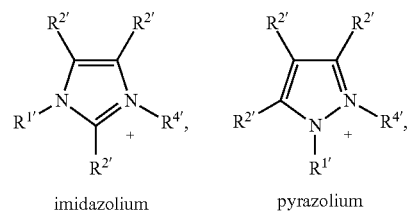

imidazolium      pyrazolium

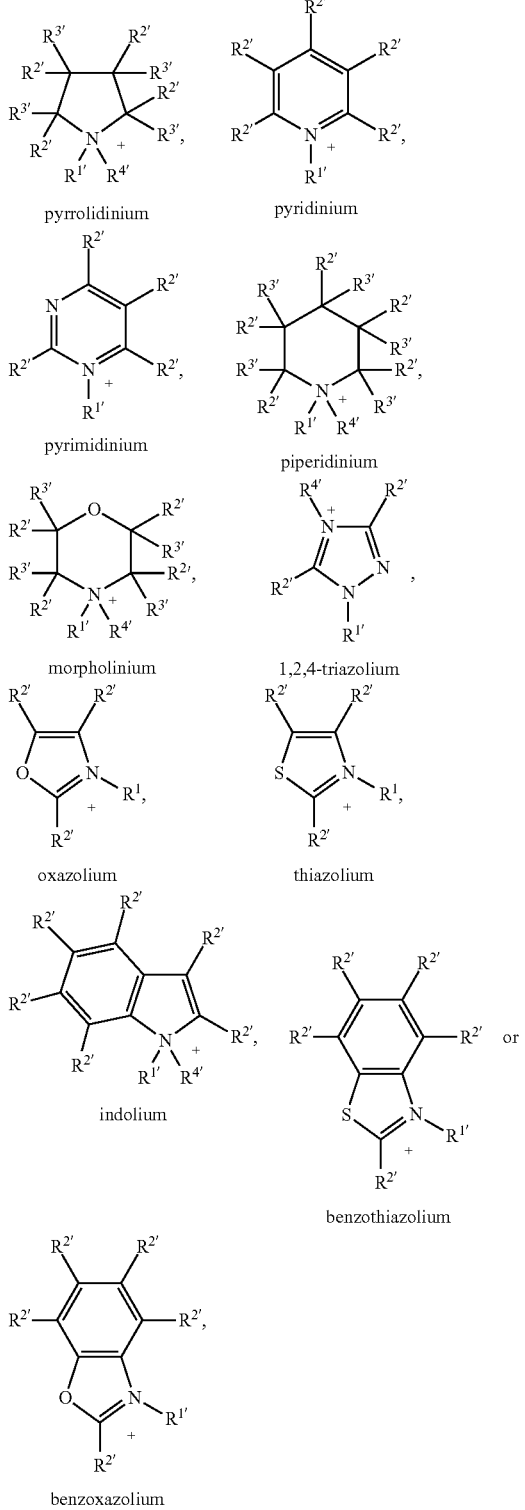

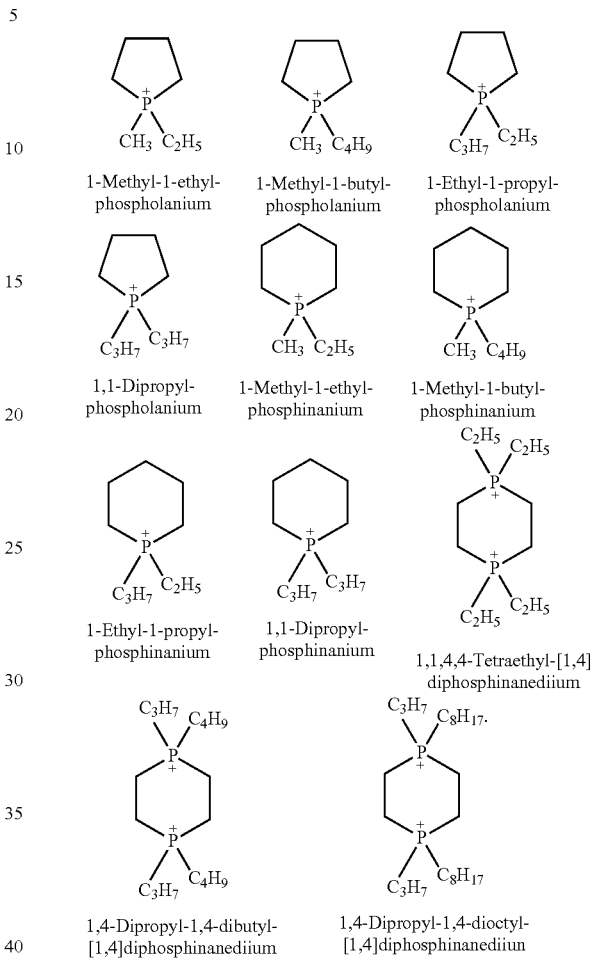

where the substituents R¹' to R⁴' each, independently of one another, have a meaning described above.

HetN⁺ is particularly preferably imidazolium, pyrrolidinium, morpholinium or pyridinium, as defined above, where the substituents R¹' to R⁴' each, independently of one another, have a meaning described above. HetN⁺ is very particularly preferably imidazolium or pyrrolidinium, where the substituents R¹' to R⁴' each, independently of one another, have a meaning described above.

HetP⁺ is particularly preferably

Preferred compounds are
1-methyl-3-methylimidazolium [(C₂F₅)₂PO]⁻,
1-ethyl-3-methylimidazolium [(C₂F₅)₂PO]⁻,
1-propyl-3-methylimidazolium [(C₂F₅)₂PO]⁻,
1-butyl-3-methylimidazolium [(C₂F₅)₂PO]⁻,
1-hexyl-3-methylimidazolium [(C₂F₅)₂PO]⁻,
1-octyl-3-methylimidazolium [(C₂F₅)₂PO]⁻,
1-(2-hydroxyethyl)-3-methylimidazolium [(C₂F₅)₂PO]⁻,
1-methyl-2,3-dimethylimidazolium [(C₂F₅)₂PO]⁻,
1-ethyl-2,3-dimethylimidazolium [(C₂F₅)₂PO]⁻,
1-propyl-2,3-dimethylimidazolium [(C₂F₅)₂PO]⁻,
1-butyl-2,3-dimethylimidazolium [(C₂F₅)₂PO]⁻,
N-butylpyridinium [(C₂F₅)₂PO]⁻,
N-ethyl-3-methylpyridinium [(C₂F₅)₂PO]⁻,
N-butyl-3-methylpyridinium [(C₂F₅)₂PO]⁻,
N-(3-hydroxypropyl)pyridinium [(C₂F₅)₂PO]⁻,
N-hexyl-4-(dimethylamino)pyridinium [(C₂F₅)₂PO]⁻,
N-ethyl-3-hydroxymethylpyridinium [(C₂F₅)₂PO]⁻,
N,N-dimethylpyrrolidinium [(C₂F₅)₂PO]⁻,
N-butyl-N-methylpyrrolidinium [(C₂F₅)₂PO]⁻,
N-(2-methoxyethyl)-N-methylpyrrolidinium [(C₂F₅)₂PO]⁻,
tetramethylammonium [(C₂F₅)₂PO]⁻,
tetrabutylammonium [(C₂F₅)₂PO]⁻,
ethyldimethylpropylammonium [(C₂F₅)₂PO]⁻,
trihexyl(tetradecyl)phosphonium [(C₂F₅)₂PO]⁻, N-(methoxyethyl)-N-methylmorpholinium [$(C_2F_5)_2PO$]$^-$,
1-methyl-3-methylimidazolium [$(C_2F_5)_2PS$]$^-$,
1-ethyl-3-methylimidazolium [$(C_2F_5)_2PS$]$^-$,
1-propyl-3-methylimidazolium [$(C_2F_5)_2PS$]$^-$,
1-butyl-3-methylimidazolium [$(C_2F_5)_2PS$]$^-$,
1-hexyl-3-methylimidazolium [$(C_2F_5)_2PS$]$^-$,
1-octyl-3-methylimidazolium [$(C_2F_5)_2PS$]$^-$,
1-methyl-3-methylimidazolium [$(C_4F_9)_2PO$]$^-$,
1-ethyl-3-methylimidazolium [$(C_4F_9)_2PO$]$^-$,
1-propyl-3-methylimidazolium [$(C_4F_9)_2PO$]$^-$,
1-butyl-3-methylimidazolium [$(C_4F_9)_2PO$]$^-$,
1-hexyl-3-methylimidazolium [$(C_4F_9)_2PO$]$^-$,
1-octyl-3-methylimidazolium [$(C_4F_9)_2PO$]$^-$,
1-(2-hydroxyethyl)-3-methylimidazolium [$(C_4F_9)_2PO$]$^-$,
1-methyl-2,3-dimethylimidazolium [$(C_4F_9)_2PO$]$^-$,
1-ethyl-2,3-dimethylimidazolium [$(C_4F_9)_2PO$]$^-$,
1-propyl-2,3-dimethylimidazolium [$(C_4F_9)_2PO$]$^-$,
1-butyl-2,3-dimethylimidazolium [$(C_4F_9)_2PO$]$^-$,
N-butylpyridinium [$(C_4F_9)_2PO$]$^-$,
N-ethyl-3-methylpyridinium [$(C_4F_9)_2PO$]$^-$,
N-butyl-3-methylpyridinium [$(C_4F_9)_2PO$]$^-$,
N-(3-hydroxypropyl)pyridinium [$(C_4F_9)_2PO$]$^-$,
N-hexyl-4-(dimethylamino)pyridinium [$(C_4F_9)_2PO$]$^-$,
N-ethyl-3-hydroxymethylpyridinium [$(C_4F_9)_2PO$]$^-$,
N,N-dimethylpyrrolidinium [$(C_4F_9)_2PO$]$^-$,
N-butyl-N-methylpyrrolidinium [$(C_4F_9)_2PO$]$^-$,
N-(2-methoxyethyl)-N-methylpyrrolidinium [$(C_4F_9)_2PO$]$^-$.

Particular combinations of features are also disclosed in the patent claims.

The present invention likewise relates to processes for the preparation of compounds of the formula I and salts of the formula II, where the substituents have a meaning indicated in claim 1 or a meaning described as preferred.

The invention therefore also relates to a process for the preparation of compounds of the formula I where A=O, X=H and n=1 and of salts of the formula II where $Y^+$=$Ag^+$, $Li^+$, $Na^+$, $K^+$, $Rb^+$, $Cs^+$ or $[NR_4]^+$ and n=1, characterised in that a tris(perfluoroalkyl)phosphine of the formula $R^1R^2R^FP$ is reacted with an inorganic or organic base, and the resultant salt of the formula II is reacted with a Brønsted acid to give the bis(perfluoroalkyl)phosphinous acid of the formula I, where $R^1$, $R^2$ have a meaning indicated in claim 1 or one of the meanings described above and $R^F$ stands for a straight-chain or branched perfluoroalkyl group having 1 to 12 C atoms or has a preferred meaning like $R^1$ or $R^2$.

The tris(perfluoroalkyl)phosphine of the formula $R^1R^2R^FP$ is preferably subjected to alkaline hydrolysis.

The alkaline hydrolysis is carried out in the presence of an aqueous solution of a base, in particular NaOH, KOH or $NH_4OH$, in an organic solvent, preferably in diethyl ether, followed by reaction with a Brønsted acid, preferably with HBr. The reaction is preferably carried out at room temperature.

Tris(perfluoroalkyl)phosphines of the formula $R^1R^2R^FP$ can be synthesised, for example, by reduction of tris(perfluoroalkyl)difluorophosphoranes [$(R^1R^2R^F)PF_2$], as described, for example, in WO 03/087113, Merck Patent GmbH.

The invention furthermore also relates to a process for the preparation of compounds of the formula I where A=O, X=H and n=1 and of the salts of the formula II, as described above, characterised in that a bis(perfluoroalkyl)phosphinyl chloride of the formula $R^1R^2P(=O)Cl$ is reacted with trialkyltin hydride and subsequently with a Brønsted acid, and the resultant bis(perfluoroalkyl)phosphinous acid $R^1R^2POH$ is reacted with a base selected from $Me_2O$, MeCN, MeOC(O)R''' or $Me_2CO_3$ or a salt KtZ to give the salt of the formula II, where Me is selected from Ag, Li, Na, K, Rb or Cs, Kt is selected from ammonium, phosphonium, tritylium, guanidinium or a heterocyclic cation containing at least one nitrogen or phosphorus atom, as described above, R''' corresponds to an alkyl group having 1 to 6 C atoms or aryl, where aryl is as defined above, and Z corresponds to an anion.

The synthesis of the bis(perfluoroalkyl)phosphinyl chloride $R^1R^2P(=O)Cl$ with substituents as described above is possible, for example, by reaction of the corresponding phosphinic acid with $PCl_5$, as described, for example, in L. M. Yagupolskii, N. V. Pavlenko, N. V. Ignatiev, G. I. Matuschecheva, V. Ya. Semenii, Zh. Obsh. Khim. (Russ.), 54 (1984), 2, 334-339.

Preference is given to the use of a Brønsted acid from the group HCl, HBr or R'''$SO_3$H, where R''' corresponds to an alkyl group having 1 to 6 C atoms or aryl; HBr is particularly preferably used.

Preference is given to the use of a trialkyltin hydride (R''')$_3$SnH, where R''' corresponds to an alkyl group having 1 to 6 C atoms or aryl, where aryl is as defined above, for example trimethyltin hydride, triethyltin hydride, tripropyltin hydride, tributyltin hydride, trihexyltin hydride, triphenyltin hydride. Tributyltin hydride is particularly preferably used.

However, the trialkyltin hydride in this reaction can alternatively also be replaced by tin hydrides of the formula (R''')$_2$SnH$_2$, where R''' in each case corresponds, independently of one another, to an alkyl group having 1 to 6 C atoms or aryl, where aryl is as defined above.

The conversion of the compound of the formula I* $R^1R^2POH$ into a salt of the formula II, as described above, can now, in order to give the salts with inorganic cations, preferably be carried out in the presence of a base $Me_2O$, MeCN, MeOC(O)R''' or $Me_2CO_3$, where Me is selected from Ag, Li, Na, K, Rb or Cs, and R''' corresponds to an alkyl group having 1 to 6 C atoms or aryl, where aryl is as defined above. Me is preferably selected from Ag, Li, Na or K.

The reaction is carried out, for example, in an organic solvent with an excess of base or acid $R^1R^2POH$, preferably with one equivalent of base. Suitable solvents are 1,2-dimethoxyethane, diethyl ether, dichloromethane, chloroform, acetonitrile, tetrahydrofuran, toluene or mixtures of the said solvents. Diethyl ether is preferably employed.

The reaction is preferably carried out at room temperature.

The conversion of the compounds of the formula I** $R^1R^2PSH$ into a salt of the formula II, as described above, can be carried out analogously to that described above.

The conversion of the compound of the formula I* $R^1R^2POH$ into a salt of the formula II, as described above, to give the salts with organic cations can now preferably be carried out in the presence of a salt KtZ, where Kt is selected from ammonium, phosphonium, tritylium, guanidinium or a heterocyclic cation containing at least one nitrogen or phosphorus atom, as described above, and Z corresponds to an anion.

The reaction is carried out, for example, in an organic solvent with an excess of salt or acid $R^1R^2POH$, preferably with equivalent amounts of the reagents.

Suitable solvents are 1,2-dimethoxyethane, diethyl ether, dichloromethane, chloroform, acetonitrile, tetrahydrofuran or mixtures of the said solvents. Diethyl ether or acetonitrile is preferably employed.

The reaction is preferably carried out at room temperature.

However, it is alternatively also possible to prepare the salts of the formula II with organic cations, as described above, from the salts of the formula II with inorganic cations.

Accordingly, the invention also relates to a process for the preparation of compounds of the formula II, as described above, where n=1 and $Y^+$ stands for ammonium, phosphonium, tritylium, guanidinium or a heterocyclic cation containing at least one nitrogen or phosphorus atom, characterised in that a salt of the formula II where n=1 and Y+ stands for Ag+, Li+, Na+, K+, Rb+ or Cs+ is reacted with a salt KtZ, where Kt is selected from ammonium, phosphonium, tritylium, guanidinium or a heterocyclic cation containing at least one nitrogen or phosphorus atom, and Z corresponds to an anion.

The reaction is carried out, for example, in an organic solvent. Suitable solvents are 1,2-dimethoxyethane, diethyl ether, acetonitrile, dichloromethane or mixtures of the said solvents. Diethyl ether, acetonitrile or dichloromethane is preferably employed.

The reaction is preferably carried out at −30° C. to room temperature, particularly preferably at room temperature.

The anion Z is preferably selected from Cl−, Br−, R⁰COO−, CF₃COO−, [BF₄]−, [PF₆]− or R″SO₃−, where R⁰ has a meaning indicated in Claim 1, and R″ denotes a straight-chain or branched alkyl group having 1 to 6 C atoms or a cycloalkyl group having 3 to 7 C atoms, which is unfluorinated, partially fluorinated or perfluorinated, or denotes unsubstituted or substituted phenyl.

The definitions of the alkyl groups, cycloalkyl groups and substituted phenyl, as described above, apply.

The anions Cl−, CH₃C(O)O−, CF₃SO₃−, [BF]− and [PF₆]− are very particularly preferably used.

The invention also relates to a process for the preparation of compounds of the formula I where A=O, X=Cl and n=0, characterised in that a bis(perfluoroalkyl)phosphinyl chloride of the formula R¹R²P(=O)Cl is reacted with trialkyltin hydride and subsequently with aryltetrachlorophosphorane, and where R¹ and R² have a meaning described above.

The synthesis of the bis(perfluoroalkyl)phosphinyl chloride R¹R²P(=O)Cl with substituents as described above has been described above.

Preference is given to the use of a trialkyltin hydride (R‴)₃SnH, where R‴ corresponds to an alkyl group having 1 to 6 C atoms or aryl, where aryl is as defined above, for example trimethyltin hydride, triethyltin hydride, tripropyltin hydride, tributyltin hydride, trihexyltin hydride, triphenyltin hydride. Tributyltin hydride is particularly preferably used.

However, the trialkyltin hydride in this reaction can alternatively also be replaced by tin hydrides of the formula (R‴)₂SnH₂, where R‴ in each case corresponds, independently of one another, to an alkyl group having 1 to 6 C atoms or aryl, where aryl is as defined above.

Aryltetrachlorophosphorane is selected, for example, from phenyltetrachlorophosphorane, tolyltetrachlorophosphorane, 1,2-phenylenephosphorus trichloride. In particular, phenyltetrachlorophosphorane is used.

The reaction is carried out, for example, in 1,6-dibromohexane with an excess of aryltetrachlorophosphorane.

The reaction is preferably carried out at room temperature.

The invention also relates to a process for the preparation of compounds of the formula I where A=O, X=Cl and n=0, characterised in that a tris(perfluoroalkyl)phosphine of the formula R¹R²R^F P is reacted with an inorganic or organic base and subsequently with a chlorinating agent, and where R¹, R² have a meaning indicated in Claim 1, and R^F denotes a straight-chain or branched perfluoroalkyl group having 1 to 12 C atoms.

Tris(perfluoroalkyl)phosphines of the formula R¹R²R^F P can be synthesised, for example, by reduction of tris(perfluoroalkyl)difluorophosphoranes [(R¹R²R^F)PF₂], as described, for example, in WO 03/087113, Merck Patent GmbH.

The inorganic base is, for example, MeOH, Me₂O or Me₂CO₃, where Me is selected from Ag, Li, Na, K, Rb or Cs. Me is preferably selected from Li, Na or K.

The organic base is, for example, [NR₄]OH, where R has one of the meanings indicated above for formula (1).

The chlorinating agent is, for example, SOCl₂, SO₂Cl₂, C(O)ClC(O)Cl, PCl₅, PCl₅ or PhPCl₄. PhPCl₄ is particularly preferably used. Ph denotes phenyl.

The reaction with a base is carried out, for example, in an organic solvent with an excess of base. Solvents which are suitable for the chlorination reaction are 1,2-dimethoxyethane, diglyme, triglyme, 1,2-dibromohexane or mixtures of the said solvents. Diglyme or 1,2-dibromohexane is preferably employed.

The reaction is preferably carried out at −20° C. to room temperature, particularly preferably at 0° C.

The invention also relates to a process for the preparation of compounds of the formula I where A=S, X=H and n=1, characterised in that a bis(perfluoroalkyl)phosphinous acid chloride of the formula R¹R²PCl is reacted with a sulfide of the formula K'₂S, where K' denotes Li, Na, K, Rb, Cs or [NH₄] and where R¹, R² have a meaning indicated in Claim 1.

The synthesis of the bis(perfluoroalkyl)phosphinous acid chlorides is carried out in accordance with the invention as described above.

Sulfides of the formula K'₂S are commercially available or can be prepared by known methods, where K' has a meaning mentioned. Na₂S or K₂S is particularly preferably used, Na₂S is very particularly preferably used.

The reaction is carried out, for example, in an organic solvent. Suitable solvents are 1,2-dimethoxyethane, diethyl ether, acetonitrile, dichloromethane or mixtures of the said solvents. Diethyl ether, acetonitrile or dichloromethane is preferably employed, dichloromethane is very particularly preferably employed.

The reaction is preferably carried out at −30° C. to room temperature, particularly preferably at room temperature.

The invention also relates to transition-metal complexes containing at least one compound of the formula I, as described above. Compounds of the formula I where A=O are preferably employed, i.e. metal-P and metal-O bonds or metal-P or metal-O bonds are preferably formed. The position of the compound of the formula I may on the one hand be terminal, on the other hand a quasi-chelate may be formed. Compounds of the formula I in which n=1 and X=H or alkyl having 1 to 18 C atoms or in which n=0 and X=H are preferably employed for the formation of the metal complexes. Compounds of the formula I in which A=O, n=1 and X=H or alkyl having 1 to 18 C atoms or in which A=O, n=0 and X=H are particularly preferably employed for the formation of the metal complexes.

Preferred transition-metal complexes conform to the formulae III to VII, where compounds of the formula I where A=O, n=1 and X=H are preferably used. It is known to the person skilled in the art also to apply these formulae III to VII to the other compounds of the formula I, as described above.

Preferred transition-metal complexes are therefore compounds of the formulae III to VII

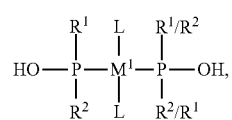

III

-continued $$\begin{array}{c} R^1/R^2 \quad R^2/R^1 \quad R^1 \quad R^2 \\ O=P \quad P-O \\ H \quad M^2 \quad M^2 \quad H, \\ O-P \quad P=O \\ R^1 \quad R^2 \quad R^1/R^2 \quad R^2/R^1 \end{array} \quad \text{IV}$$

$$\begin{array}{c} OH \\ | \\ R^1-P-M^1L_n, \\ | \\ R^2 \end{array} \quad \text{V}$$

$$\begin{array}{c} R^1/R^2 \quad R^2/R^1, \\ O=P \\ H \quad M^2L_n \\ O-P \\ R^1 \quad R^2 \end{array} \quad \text{VI}$$

$$\left[ \begin{array}{c} R^1 \\ \diagdown \\ P-O \\ \diagup \\ R^2 \end{array} \right]_m \!\! - M^2 - L_n, \quad \text{VII}$$

where $M^1$ and $M^2$ are transition metals selected from the group Pt, Pd, Rh, Ir, Ru, Ni, Co, Fe, Au, Os, Ti, Zr, V, Cr, Mn, Mo, W, Re, Y, Nd, Yb, Sm, Tb or La, L is an anionic, neutral or cationically charged ligand, $R^1$ and $R^2$ each stand, independently of one another, for straight-chain or branched perfluoroalkyl groups having 2 to 12 C atoms, and $R^1/R^2$ in formula IV stands for $R^1$ or $R^2$ or $R^2/R^1$ in formula IV stands for $R^2$ or $R^1$ and $R^0$ stands for a straight-chain or branched alkyl group having 1 to 8 C atoms, and n denotes the number of ligands necessary to saturate the valences of $M^1$ or $M^2$, and where in formula VII, the sum n+m corresponds to the coordination number of the metal $M^2$.

In formula VII, n may also be equal to 0.

$M^1$ and $M^2$ are preferably selected from Pt, Pd, Rh, Ru and Ni, very particularly preferably Pd and Pt or Pd or Pt.

Ligands for metal complexes according to the invention can be anionic, neutral or cationically charged ligands which are known to the person skilled in the art in the area of metal complexes. Examples of ligands L are preferably selected from H, OH, Cl, =O, CO, CH$_3$CN, R$^0$COO, PR$^0$$_3$, phosphinous acid, phosphinites, NR$^0$$_3$, dialkyl ethers, cyclic ethers, including tetrahydrofuran and dioxane, a double bond, a triple bond, aryl, cyclopentadienyl, or heterocyclic ligands, for example heterocyclic carbenes, or "pincer ligands"; L is very particularly preferably Cl.

Pincer ligands are known, for example, from C. J. Moulton et al, J. Chem. Soc., Dalton Trans. 1976, 1020-1024, M. E. van der Boom, et al, Chem. Rev. 2003, 103, 1759-1792, and are known to the person skilled in the art in the area of catalysis. Pincer complexes consist of a metal centre and a tridentate ligand, which is connected to the metal centre via at least one metal-carbon σ bond. Examples are planar aryl compounds.

The substituents $R^1$, $R^2$, $R^0$ have a meaning indicated above or a preferred meaning indicated above.

The type of complex, whether a mononuclear complex of the formula III, V, VI or VII or a polynuclear complex of the formula IV, depends on the reaction conditions, metal cations and also ligands selected. It is also possible for mixtures of the said transition-metal complexes to be formed and used.

Both the transition-metal complexes of the formulae III to VII and mixtures thereof are highly suitable for homogeneous catalysis. Mixtures are therefore mixtures of the complexes of the formula III with formula IV, V, VI or VII, mixtures of the complexes IV with formula V, VI or VII, mixtures of the complexes of the formula V with formula VI or VII, mixtures of the formula VI and VII, three-component combinations of the complexes of the formulae III to VII or four-component combinations of the complexes of the formulae III to VII.

Mixtures in which the substituents of the formulae III to VII, as described above, are identical or different may also be advantageous.

The metal complexes of the formula III, IV, V, VI or VII according to the invention and mixtures thereof, as described above, are preferably advantageous for the following reactions:

Heck reaction, Suzuki reaction, Hiyama reaction with siloxanes, KumadaTorriu reaction, Negishi reaction, Negishi-Stille reaction, Sonogashira reaction, C—S coupling reaction, C—N coupling reaction, C—O coupling reaction, C—B coupling reaction, C—P coupling reaction, decarboxylating biaryl coupling, hydroformylation or a C—H activation, polymerisation, or oxidation and hydrogenation reactions.

Details of the individual reaction types are indicated below:

Heck Reaction:

$$R\!\!-\!\!\!\bigcirc\!\!\!-\!\!X + \diagup\!\!\!\diagdown\!\!R^1 \xrightarrow[\text{solvent}]{\text{cat.}} R\!\!-\!\!\!\bigcirc\!\!\!-\!\!\diagup\!\!\!\diagdown\!\!R^1$$

base

Mechanism[1]
  starting materials: 2-chloroquinoline, $R^1$=CO$_2$t-Bu->cat.: POPd, POPd1, POPd2[1]
  $R^1$=CO$_2$t-Bu->cat.: POPd[2]
  $R^1$=C$_6$H$_5$, CO$_2$Bu->cat.: Pd(OAc)$_2$/carbene[3]
  $R^1$=Ph, CO$_2$n-Bu->cat.: PdHAP-1[4]
  $R^1$=CO$_2$n-Bu->cat.: [Pd(C$_3$H$_5$)Cl]$_2$/tedicyp[5,6]
  $R^1$=CO$_2$n-Bu, CO$_2$t-Bu->cat.: Pd$_2$(dba)$_3$[7]
  $R^1$=CO$_2$n-Bu,->cat.: Pd/carbene complex[8]
  Pd catalysis in ionic liquids[9]
  Bases: K$_2$CO$_3$, Na$_2$CO$_3$, Cs$_2$CO$_3$, NaOAc, Cy$_2$NMe, Et$_3$N, t-BuOK, t-BuONa, DABCO.
  Solvents: DMF, dioxane, DMA, NMP, toluene.
  Temperature: reflux.

1 J. P. Knowles, A. Whiting, *Org. & Biomol. Chem.*, 2007, 5, 31-44.
2 C. Wolf, R. Lerebours, *J. Org. Chem.*, 2003, 68, 7077-7084.
3 G. Y. Li, G. Zheng, A. F. Noonan, *J. Org. Chem.*, 2001, 66, 8677-8681.
4 V. Caló, R. Del Sole, A. Nacci, E. Schingaro, F. Scordari, *Eur. J. Org. Chem.*, 2000, 2000, 869-871.

5 K. Mori, K. Yamaguchi, T. Hara, T. Mizugaki, K. Ebitani, K. Kaneda, *J. Am. Chem. Soc.*, 2002, 124, 11572-11573.

6 M. Feuerstein, H. Doucet, M. Santelli, *J. Org. Chem.*, 2001, 66, 5923-5925.

7 M. Feuerstein, H. Doucet, M. Santelli, *Synlett.*, 2001, 12, 1980-1982.

8 A. H. M. de Vries, J. M. C. A. Mulders, J. H. M. Mommers, H. J. W. Henderickx, J. G. de Vries, *Org. Lett.*, 2003, 5, 3285-3288.

9 Ai-E Wang, Jian-Hua Xie, Li-Xin Wang, Qi-Lin Zhou, *Tetrahedron*, 2005, 61, 259-266.

10 R. Singh, M. Sharma, R. Mamgain, D. S. Rawat, *J. Braz. Chem. Soc.*, 2008, 19, 357-379.

Suzuki Reaction:

reaction at room temperature->cat.: $Pd_2(dba)_3/P(t-Bu)_3$[11]

reaction at room temperature->cat.: $[Cl_2Pd(COD)]$/piperazine[12]

R=2-fluorobenzene->cat.: $Pd(OAc)_2$/phosphine ligand[13]

Ar=$C_6F_5$->cat.: $Pd_2(dba)_3/P(t-Bu)_3$[14]

Ar=$C_6F_5$+dibromothiophene->$Pd(PPh_3)_4$[15]

Ar=Ph->cat.: POPd[16]

nickel catalyst $[Ni(cod)_2]/PCy_3$ (cyclohexane)[17]

nickel catalyst $[Ni(dppf)Cl_2]$[18]

R=benzylic phosphate->cat.: $Pd(OAc)_2/PPh_3$[19]

review article, compare with Stille and $Si(OMe)_3$[20]

11 A. F. Littke, C. Dai, G. C. Fu, *J. Am. Chem. Soc.*, 2000, 122, 4020-4028.

12 S. Mohanty, D. Suresh, M. S. Balakrishna, J. T. Mague, *Tetrahedron*, 2008, 64, 240-247.

13 J. Kingston, J. Verkade, *J. Org. Chem.*, 2007, 72, 2816-2822.

14 T. Korenaga, T. Kosaki, R. Fukumura, T. Ema, T. Sakai, *Org. Lett.*, 2005, 7, 4915-4917.

15 K. Takimiya, N. Niihara, T. Otsubo, *Synthesis*, 2005, 10, 1589-1592.

16 G. Y. Li, *J. Angew. Chem.*, 2001, 113, 1561-1564.

17 M. Tobisu, T. Shimasaki, N. Chatani, *Angew. Chem.*, 2008, 120, 4944-4947.

18 A. F. Indolese, *Tetrahedron Lett.*, 1997, 38, 3513-3516.

19 M. McLaughlin, *Org. Lett.*, 2005, 7, 4875-4878.

20 C. J. Handy, A. S. Manoso, W. T. McElroy, W. M. Seganish, P. DeShong, *Tetrahedron*, 2005, 61, 12201-12225.

->variant with perfluoroalkyltrifluoroborates; cat.: $Pd(OAc)_2/PPh_3$[21] Further papers-> cat.: $[Pd(dppf)Cl_2]$[22]

vinyl trifluoroborate and benzyl 3,5-bis(benzyloxy)-4-bromobenzoate->cat.: $[Pd(dppf)Cl_2]$[23]

cat.: $Pd(OAc)_2$[24]

->review[25]

Bases: $K_2CO_3$, $Na_2CO_3$, $Cs_2CO_3$, CsF, KF, t-BuOK, t-BuONa, NaOH, KOH, $K_3PO_4$.

Solvents: dioxane, THF, MeOH, $Me_2CHOH$, DME, toluene, DMF, DMA, NMP.

Temperature: RT to reflux.

20 H.-J. Frohn, N. Yu. Adonin, V. V. Bardin, V. F. Starichenko, *Tetrahedron Lett.*, 2002, 43, 8111-8114.

22 G. W. Kabalka, G. Dong, B. Venkataiah, *Tetrahedron Lett.*, 2004, 45, 5139-5141.

23 R. R. Carter, J. K. Wyatt, *Tetrahedron Lett.*, 2006, 47, 6091-6094.

24 L. Joucla, G. Cusati, C. Pinel, L. Djakovitch, *Tetrahedron Lett.*, 2008, 49, 4738-4741.

25 S. Darses, J.-P. Genet, *Chem. Rev.*, 2008, 108, 288-325.

Hyama Reaction with Siloxanes:

reaction with aryl halides in water->cat.: POPd1[26]
starting material: 4-haloquinoline->cat. POPd, POPd1, POPd2[27]
review article, compare with Stille and Suzuki[20]
Bases: TBAF, $K_2CO_3$, $Na_2CO_3$, $Cs_2CO_3$, NaOH, KOH, $K_3PO_4$.
Solvents: DMF, MeCN, i-PrOH, EtOAc, DMA, THF.
Temperature: reflux.

26 C. Wolf, R. Lerebours, *Org. Lett.*, 2004, 6, 1147-1150.
27 C. Wolf, R. Lerebours, E. H. Tanzini, *Synthesis*, 2003, 13, 2069-2073.

Kumada-Toriu reaction

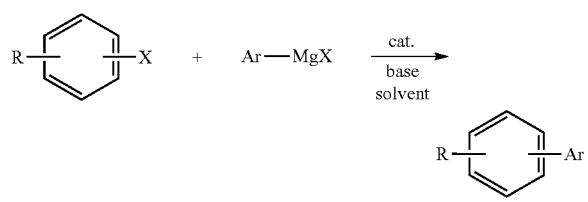

cat.: POPd, POPd1[28]

28 G. Y. Li, *J. Organomet. Chem.*, 2002, 653, 63-68.

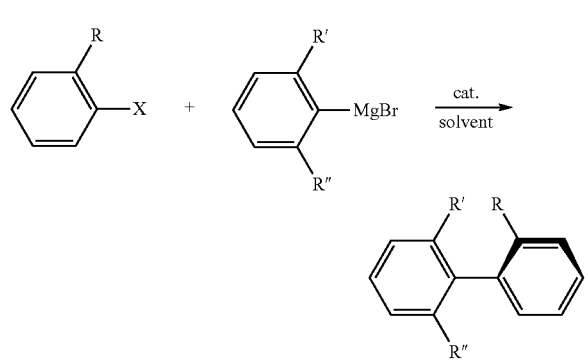

R=Me, isopropyl, OMe; R'=Me, cyclohexane, OMe, R"=Me, H, OMe; or 2-MgBr-terphenyl->cat.: POPd, $Ni(COD)_2/(t-Bu)_2P(O)H^{29}$
Solvents: THF, dioxane, $Et_2O$, DME.
Temperature: RT or reflux 29 C. Wolf, H. Xu, *J. Org. Chem.*, 2008, 73, 162-167.

Negishi Reaction

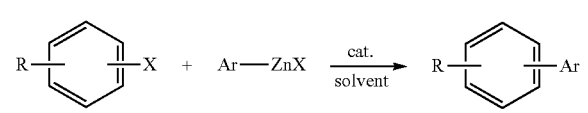

Ar=Ph, X=$C_1$->cat.: POPd, POPd2[37]
Ar=alkyl, aryl, alkenyl->cat.: $Pd_2(dba)_3/PCyp_3$ (note: Cyp=cyclopentyl)[30]
R=2,4,6-isopropyl, Ar=OMe->cat. $Pd_2(dba)_3$/S-phos. or Ru-phos. etc.[31]
Solvents: NMP, THF, toluene, DME.
Temperature: room temperature to reflux 30 J. Zhou, G. C. Fu, *J. Am. Chem. Soc.*, 2003, 125, 12527-12530.
31 J. E. Milne, S. L. Buchwald, *J. Am. Chem. Soc.*, 2004, 126, 13028-13032.

Negishi-Stille Reaction

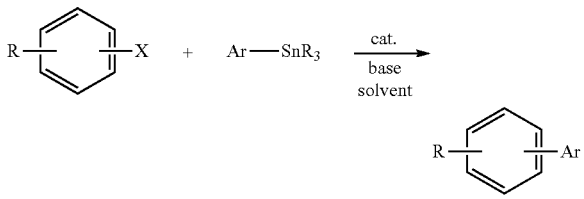

starting material: 4-haloquinoline->cat.: POPd, POPd1, POPd2[2,32]
one-pot synthesis from Stille and Heck reaction[33]
Bases: $R_3N$.
Solvents: dioxane, DMF, THF.
Temperature: reflux.

32 C. Wolf, R. Lerebours, *J. Org. Chem.*, 2003, 68, 7551-7554.
33 P. von Zerschwitz, F. Petry, A. de Meijere, *Chem. Eur. J.*, 2001, 7, 4035-4046.

Sonogashira Reaction

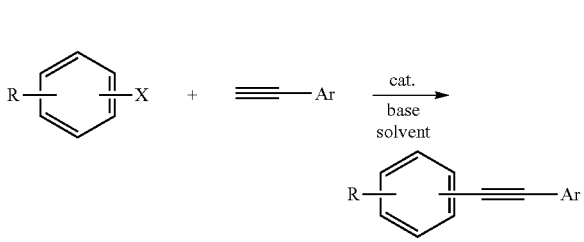

use of various sterically hindering phosphine ligands and calculation of the kinetics[34]
Sonogashira reaction in water[35]
Sonogashira reaction in ionic liquid[36]
Bases: amines, pyrrolidine, NaOH, KOH, $K_2CO_3$, $Cs_2CO_3$, $Na_2CO_3$.
Solvents: dioxane, DMF, 1-n-butyl-3-methylimidazolium tetrafluoroborate.
Temperature: reflux 34 M. R. an der Heiden, H. Plenio, S. Immel, E. Burello, G. Rothenberg, H. C. J. Hoefsloot, *Chem. Eur. J.*, 2008, 14, 2857-2866.
35 C. Wolf, R. Lerebours, *Org. Biomol. Chem.*, 2004, 2, 2161.
36 J.-C. Hierso, J. Boudon, M. Picquet, P. Meunier, *Chem. Eur. J.*, 2007, 13, 583-587.

C—S Coupling Reaction:

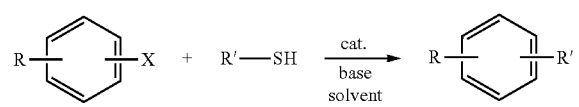

R'=t-Bu;->cat.: POPd[16]
R'=alkyl, Ph->cat.: POPd, POPd1[3,2,37]
Bases: t-BuOK, t-BuONa, $Cy_2NMe$, $Et_3N$, $K_2CO_3$, $Cs_2CO_3$, $Na_2CO_3$.
Solvents: DMSO, dioxane, toluene, DME.
Temperature: RT to reflux.

37 G. Y. Li, *J. Org. Chem.*, 2002, 67, 3643-3650.

C—N Coupling Reaction:

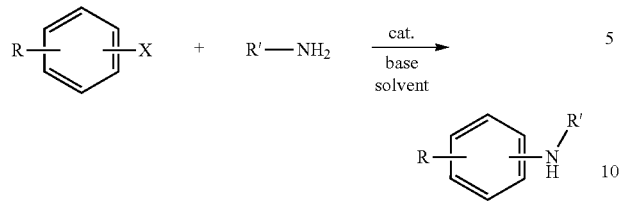

starting material: 4-haloquinoline; R'=Ph->cat.: POPd, POPd1, POPd2[2,3,16]

copper catalyst at room temperature [CuI/N,N-diethylsalicylamide][38]

38 A. Shafir, S. L. Buchwald, *J. Am. Chem. Soc.,* 2006, 8742-8473.

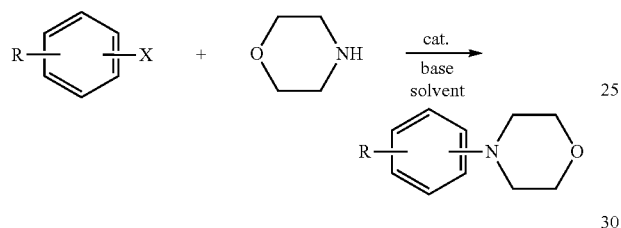

reaction at room temperature->cat.: Pd(OAc)$_2$/phosphine ligand[39]

39 Ch. V. Reddy, J. V. Kingston, J. G. Verkade, *J. Org. Chem.,* 2008, 73, 3047-3062.

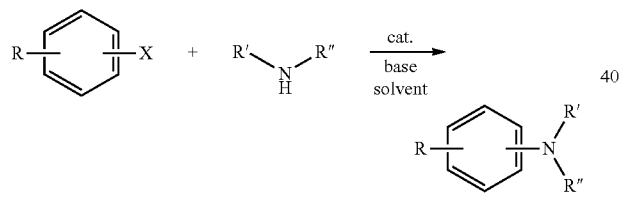

reaction at room temperature; R'=Me, R''=Ph->cat.: Pd(OAc)$_2$/phosphine ligand[39]

reaction at 80° C., Ph->cat.: Pd(OAc)$_2$/phosphine ligand[39]

nickel catalyst [trans-haloarylbis(triphenylphosphine)nickel(II)][40]

reaction at room temperature->cat.: Pd(OAc)$_2$/phosphine ligand[39]

40 C. Chen, L.-M. Yang, *J. Org. Chem.,* 2007, 72, 6324-6327.

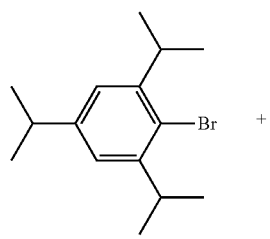

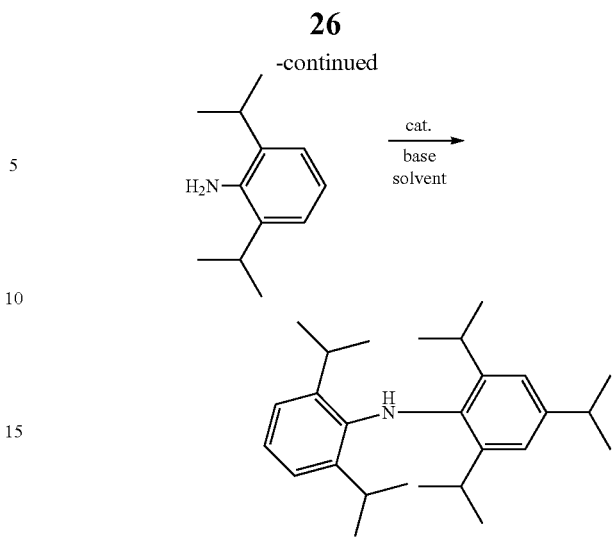

reaction at room temperature->cat.: Pd(OAc)$_2$/phosphine ligand[39]

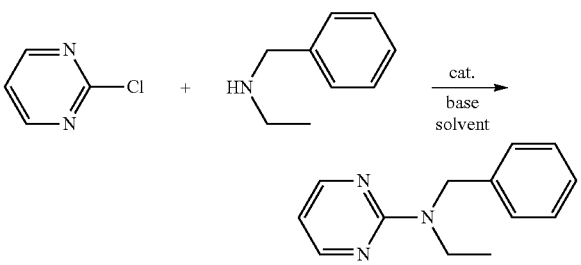

reaction at room temperature->cat.: Pd(OAc)$_2$/phosphine ligand[39]

Bases: t-BuOK, t-BuONa, R$_3$N, NaOH, KOH, K$_2$CO$_3$, Cs$_2$CO$_3$, Na$_2$CO$_3$.

Solvents: DMSO, dioxane, toluene, DMF.

Temperature: RT to reflux.

C—O Coupling Reaction:

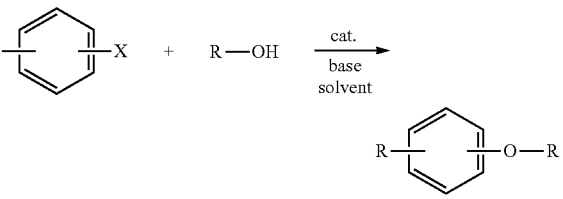

C—O coupling with subsequent Claisen rearrangement->cat.: Cu/amine ligand [1,10-phenanthroline][41]

C—O coupling in the case of primary and secondary alcohols->cat.: Pd(OAc)$_2$/phosphine ligands [note: Strem company][42]

C—N vs. C—O coupling in the case of amino alcohols->selectivity in the copper-catalysed synthesis [CuI/diketone][43]

41 G. Nordmann, S. L. Buchwald, *J. Am. Chem. Soc.,* 2003, 125, 4978-4979.

42 A. V. Vorogushin, X. Huang, S. L. Buchwald, *J. Am. Chem. Soc.,* 2005, 127, 8146-8149.

43 A. Shafir, P. A. Lichtor, S. L. Buchwald, *J. Am. Chem. Soc.,* 2007, 129, 3490-3491.

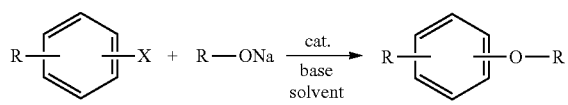

X=Br, Cl; R=t-Bu->cat.: $Pd_2(dba)_3/P(t-Bu)_3$, or phosphine ligand, which is not air-stable[44]

Bases: t-BuOK, t-BuONa, NaOH, KOH, $K_2CO_3$, $Cs_2CO_3$, $Na_2CO_3$.

Solvents: DMSO, dioxane, toluene, DMF, DME, o-xylene.

Temperature: reflux.

44 G. Mann, C. Incarvito, A. L. Rheingold, J. F. Hartwig, *J. Am. Chem. Soc.*, 1999, 121, 3224-3225.

C—B Coupling Reaction:

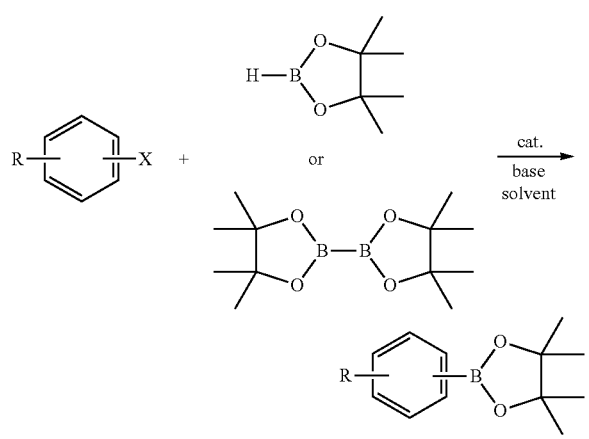

starting material: $R^1R^2N$—$BH_2$ $R^1$=$R^2$=iPr->cat.: $(PPh_3)_2PdCl_2$[45]

45 L. Euzenat, D. Horhant, Y. Ribourdouille, C. Duriez, G. Alcaraz, M. Vaultier, *Chem. Commun.*, 2003, 2280-2281.

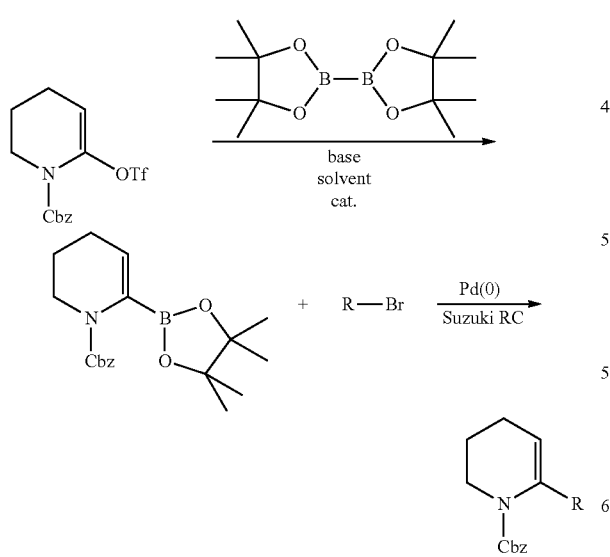

starting material: lactam derivative; subsequent reaction in the Suzuki reaction[46]

46 A. Ferrali, A. Guarna, F. Lo Galbo, E. G. Occhiato, *Tetrahedron Lett.*, 2004, 45, 5271-5274.

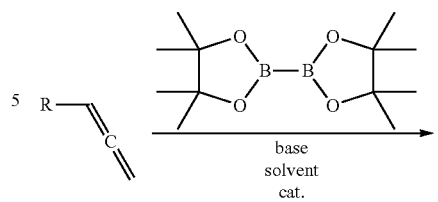

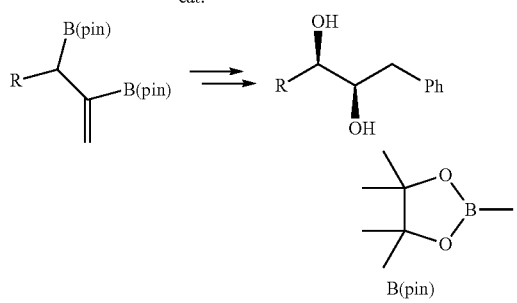

starting material: diene->cat.: $Pd_2(dba)_3$/phosphine ligand[47]

Bases: NaOH, KOH, $K_2CO_3$, $Cs_2CO_3$, $Na_2CO_3$, $K_3PO_4$, $R_3N$.

Solvents: dioxane, toluene, DMF, DME.

Temperature: reflux

47 N. F. Pelz, J. P. Morken, *Org. Lett.*, 2006, 8, 4557-4559.

C—P Coupling Reaction:

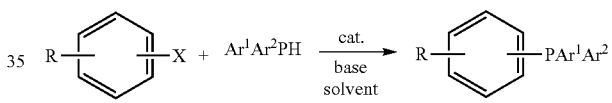

starting material: 2,6-dibromopyridine->cat.: $Pd(OAc)_2$[48]

$Ar^1=Ar^2=Ph$->cat.: $Pd(OAc)_2$; microwaves[49]

$Ar^1=2-(CF_3)C_6H_4$->cat.: $Pd(OAc)_2$/phosphine ligand[50]

Bases: $R_3N$, N-Me-piperidine, KOAc, NaOAc, DABCO, $K_2CO_3$, $Cs_2CO_3$, $Na_2CO_3$.

Solvents: toluene, DMF, DMA, acetonitrile, methanol, NMP.

Temperature: reflux

48 O. Herd, A. HeBler, M. Hingst, M. Tepper, O, Stelzer, *J. Organomet. Chem.*, 1996, 522, 69-76.

49 A. Stadler, C. O. Kappe, *Org. Lett.*, 2002, 4, 3541-3543.

50 C. Korff, G. Helmchen, *Chem. Commun.*, 2004, 530-531.

Decarboxylating biaryl coupling:

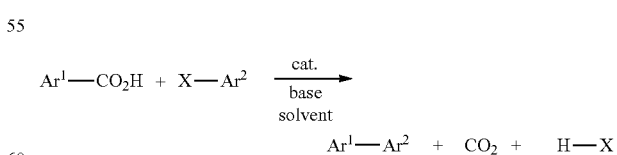

use of various heteroaromatic carboxylic acids->cat.: Pd/P$(t-Bu)_3$[51]

51 P. Forgione, M.-C. Brochu, M. St-Onge, K. H. Thesen, M. D. Bailey, F. Bilodeau, *J. Am. Chem. Soc.*, 2006, 128, 11350-11351.

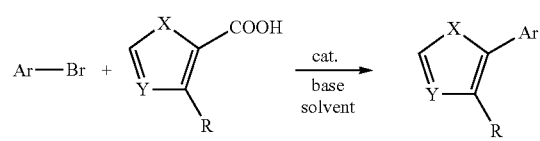

X=O,N,S
Y=CH, N
->cat.: Pd/P(t-Bu)$_3$[52]

Advantage over C—H activation is the regioselectivity, which is ensured by the carbonyl function.

Bases: $K_2CO_3$, $Cs_2CO_3$, $Na_2CO_3$, $K_3PO_4$, $R_3N$.
Solvents: NMP, toluene, DMF, DME.
Temperature: reflux 52 O. Baudoin, *Angew. Chem.*, 2007, 119, 1395-1397.

Hydroformylation:

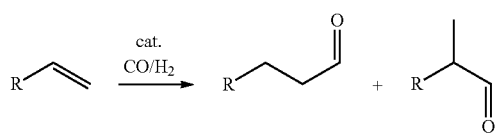

cat. Rh(I)/BISBI, BIPHEPHOS, XANTPHOS[53]
characterisation of the intermediates->Pt/Ph$_2$POH[54]
long-chain α-olefins>C$_7$; H$_2$O/organic solvent two-phase system->cat.: phosphonate/phosphine complex[55]
stereoselective hydroformylation of enamides->cat.: Rh(acac)(CO)$_2$/phosphite ligands[56]
investigations of phosphites having various steric and electronic properties (Ex.: 4-CF$_3$—C$_6$H$_4$); use of supercritical CO$_2$->cat.: Rh/phosphites[57]
hydroformylation in ionic liquids[58]
Solvents: toluene, H$_2$O.
Temperature: 60-120° C.
Other cond.: 20-60 bar CO$_2$/H$_2$ 53 B. Breit, *Acc. Chem. Res.*, 2003, 36, 264-275.
P. W. N. M. van Leeuwen, C. F. Roobeek, J. H. G. Frijns, G. Orpen, *Organometallics*, 1990, 9, 1211-1222.
55 S. Bischoff, M. Kant, *Ind. Eng. Chem. Res.*, 2000, 39, 4908-4913.
56 O, Saidi, J. Ruan, D. Vinci, X. Wu, J. Xiao, *Tetrahedron-Lett.*, 2008, 49, 3516-3519.
57 C. T. Estorach, A. Orej'on, A. M. Masdeu-Bult'o, *Green Chemistry*, 2008, 10, 545-552.
58 M. Naumann, A. Riisager, *Chem. Rev.*, 2008, 108, 1474-1497.

C—H Activation:

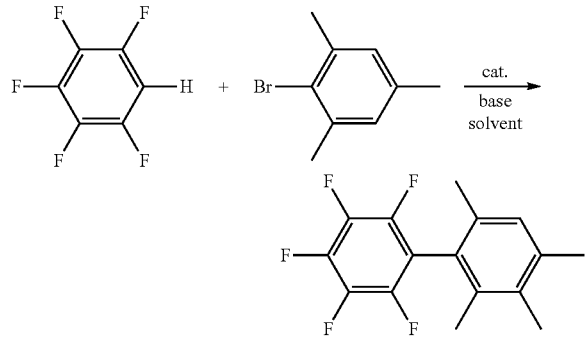

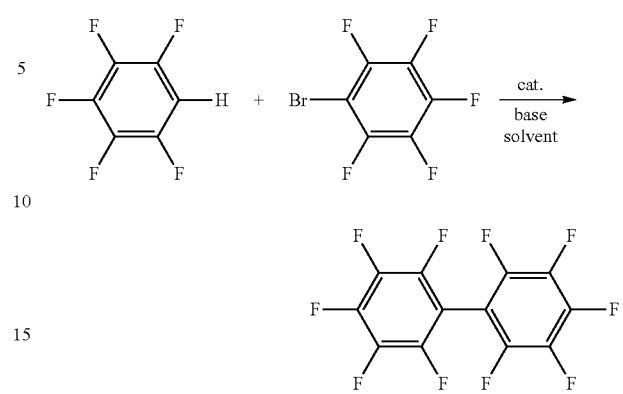

starting materials: pentafluorobenzene, 2,3,5,6-tetrafluoropyridine, 1,3,5-trifluorobenzene, etc.->cat.: Pd(OAc)$_2$/S-phos.[59] [further papers][60,61]

gold-catalysed reactions starting from C—H activation[62]

Bases: $K_2CO_3$, $Cs_2CO_3$, $Na_2CO_3$, $R_3N$, KOt-Bu, NaOt-Bu.
Solvents: toluene, DMF, DME, DMA, i-PrOAc, EtOAc.
Temperature: reflux.

59 M. Lafrance, D. Shore, K. Fagnou, *Org. Lett.*, 2006, 8, 5097-5100.
60 M. Lafrance, C. N. Rowley, T. K. Woo, K. Fagnou, *J. Am. Chem. Soc.*, 2006, 128, 8754-8756.
61 L.-C. Campeau, M. Parisien, A. Jean, K. Fagnou, *J. Am. Chem. Soc.*, 2006, 128, 581-590.
62 R. Skouta, C.-J. Li, *Tetrahedron*, 2008, 64, 4917-4938.

Structures of the catalysts used in the literature:

POPd

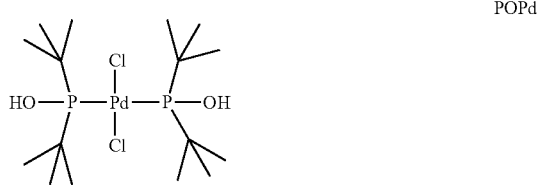

POPd1

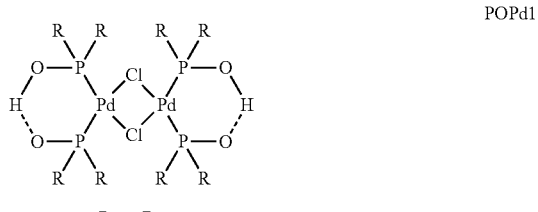

R = t-Bu

POPd2

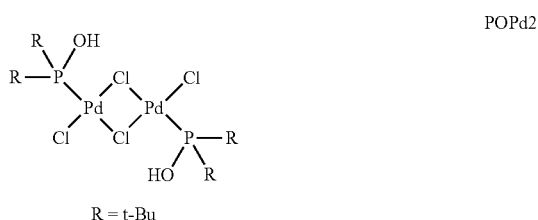

R = t-Bu

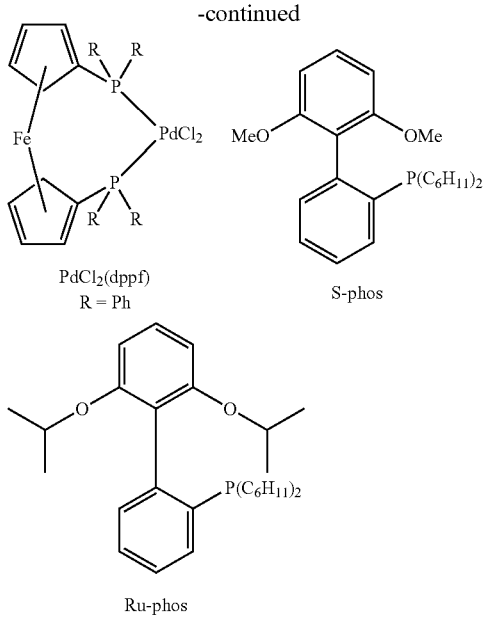

PdCl₂(dppf)
R = Ph

S-phos

Ru-phos

The invention also relates to a process for the preparation of the transition-metal complexes of the formulae III, IV, V, VI and VII, as described above, characterised in that a compound of the formula I, as described above or as preferably described, particularly preferably where X=H and n=1, is reacted with a precursor compound containing the transition metal, in particular a compound $M^1L_2$ or $M^2L_2$, where $M^1$, $M^2$ and L have one of the meanings indicated above or the preferred meanings.

The reaction is carried out, for example, in an organic solvent. However, the reaction can also be carried out without a solvent. Suitable solvents are diethyl ether, 1,2-dimethoxyethane, acetonitrile or tetrahydrofuran. Diethyl ether is preferably employed.

The reaction is carried out at −30° C. to the boiling point of the solvent, preferably at 0° C. to room temperature, particularly preferably at room temperature.

The reaction is preferably carried out using dried solvents and under inert-gas conditions, i.e. under inert gases, such as argon or nitrogen.

The invention also relates to the use of complexes of the formula III, IV, V, VI or VII and mixtures thereof as catalyst for the treatment of surfaces or for the production of nanoparticles of the corresponding metal $M^1$ or $M^2$.

Nanoparticles are synthesised by the reduction, thermolysis, photolysis or electrolysis of complexes of the formula III, IV, V, VI or VII or salts of the formula II in solvents, for example in organic solvents or ionic liquids, or in an inert liquid or gaseous phase, or without a solvent (J. Krämer et al., Ionische Flüssigkeiten als Templat für Nanosynthesen [Ionic Liquids as Template for Nanosyntheses], GIT Laboratory Journal, No. 4, 2008, pp. 400-403; E. Redel et al., First Correlation of Nanoparticles Size-Dependent Formation with Ionic Liquid Anion Molecular Volume, Inorganic Chemistry, 47, 2008, pp. 14-16).

Furthermore, the salts of the formula II, as described above, where $Ag^+$, $Li^+$, $Na^+$, $K^+$, $Rb^+$ or $Cs^+$ is excluded for $Y^+$, preferably form an ionic liquid.

Areas of application of ionic liquids are, for example, the use as solvent or solvent additive, as phase-transfer catalyst, as extractant, as heat-transfer medium, as surface-active substance, as plasticiser, as antistatic, as flameproofing agent or as conductive salt or as additive for electrochemical and photoelectrochemical cells.

The present invention therefore furthermore relates to the use of salts of the formula II, as described above, where $Ag^+$, $Li^+$, $Na^+$, $K^+$, $Rb^+$ or $Cs^+$ is excluded for $Y^+$, as solvent or solvent additive, as phase-transfer catalyst, as extractant, as heat-transfer medium, as surface-active substance, as plasticiser, as antistatic, as flameproofing agent or as conductive salt or as additive for electrochemical and photoelectrochemical cells.

In the case of the use as solvent, this is suitable in any type of reaction known to the person skilled in the art, for example for transition-metal- or enzyme-catalysed reactions, such as, for example, hydroformylation reactions, oligomerisation reactions, esterifications or isomerisation reactions, where the said list is not definitive.

On use as extractant, the ionic liquid can be employed for separating off reaction products, but also for separating off impurities, depending on the solubility of the respective component in the ionic liquid. In addition, the ionic liquids can also serve as separating agents in the separation of a plurality of components, for example in the distillative separation of a plurality of components of a mixture.

Further possible applications are the use as plasticiser in polymer materials, as flameproofing agent for a number of materials or applications and as conductive salt or additive in various electrochemical cells and applications, for example in galvanic cells, in capacitors or in fuel cells.

Further areas of application of ionic liquids, i.e. here the salts of the formula II, as defined above, are the use as solvent for carbohydrate-containing solids, in particular biopolymers and derivatives or decomposition products thereof. In addition, some preferred salts of the formula II may be suitable as grease, operating fluids for machines, such as, for example, compressors, pumps or hydraulic devices. Furthermore, some preferred salts of the formula II may also be suitable for electro-optical cells, for example in sensors.

Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

The NMR spectra were measured on solutions in deuterated solvents at 20° C. in a Bruker Avance 300 spectrometer with a 5 mm ¹H/BB broadband probe with deuterium lock, unless indicated in the examples. The measurement frequencies of the various nuclei are: ¹H: 300.13 MHz, ¹⁹F: 282.41 MHz, ³¹P: 121.49 MHz and ¹³C, 75.47 MHz. The referencing method is indicated separately for each specimen or data set.

Example 1

Bis(pentafluoroethyl)phosphinous acid

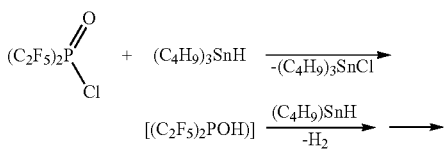

-continued

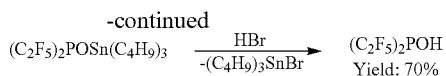

4.79 g (16.5 mmol) of $(C_4H_9)_3SnH$ are dissolved in 1,6-dibromohexane, and the solution is degassed (vacuum) for 15 min. 2.20 g (6.9 mmol) of bis(pentafluoroethyl)phosphinyl chloride, $(C_2F_5)_2P(O)Cl$, are added. The solution is stirred at room temperature for 30 min, and the volatile products are subsequently removed in vacuo. The residue is stirred at room temperature under an HBr atmosphere (7.3 mmol) for 20 min, and the volatile compounds are then removed under dynamic vacuum conditions. Three cold traps having a different temperature are employed, at −30° C., −78° C. and −196° C. At −78° C., an uncoloured liquid is obtained and identified as bis(pentafluoroethyl)phosphinous acid. The compound is stable at room temperature under inert-gas conditions.

$^1$H NMR ($C_6D_6$; standard: TMS), δ, ppm: 2.2 s.
$^{19}$F NMR ($CDCl_3$; standard: $CCl_3F$), δ, ppm: −81.9 d, m ($2CF_3$), −123.4 d, d, m ($CF_2$, $F_A$), −124.5 d, d, m ($CF_2$, $F_B$), $^2J_{P,F(A)}$=71 Hz, $^2J_{P,F(B)}$=57 Hz, $^2J_{F(A),F(B)}$=320 Hz, $^3J_{P,F}$=15 Hz.
$^{31}$P NMR ($CDCl_3$; standard: 85% $H_3PO_4$), δ, ppm: 84.4 m.

Example 2

Bis(pentafluoroethyl)phosphinous acid chloride or synonymously bis(pentafluoroethyl)chlorophosphine Method A:

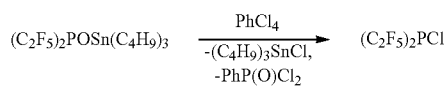

2.5 g (7.8 mmol) of bis(pentafluoroethyl)phosphinyl chloride, $(C_2F_5)_2P(O)Cl$, are added to a solution of 4.9 g (16.8 mmol) of $(C_4H_9)_3SnH$ in 1,6-dibromohexane. The reaction mixture is stirred at room temperature for one hour, and the volatile compounds are then removed in vacuo. 1.24 g (5.0 mmol) of $C_6H_5Cl_4$ are added, and the mixture is stirred at room temperature for 20 min. The volatile compounds are removed under dynamic vacuum conditions. Three cold traps are employed: −30° C., −78° C. and −196° C. The cold trap at −196° C. contains the colourless liquid, identified as bis(pentafluoroethyl)phosphinous acid chloride, $(C_2F_5)_2PCl$. The compound is stable at room temperature under inert-gas conditions.

$^{19}$F NMR (diethyl ether; standard: $CCl_3F$), δ, ppm: −80.8 d,m ($2CF_3$), −116.5 m ($2CF_2$, A,B system), $^3J_{P,F}$=14 Hz.
$^{31}$P NMR (diethyl ether; standard: 85% $H_3PO_4$), δ, ppm: 60.4 m.

Method B:

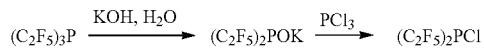

A solution of 1.16 g (3.0 mmol) of tris(pentafluoroethyl) phosphine, $(C_2F_5)_3P$, in 1,2-dimethoxyethane is treated with an excess (6 mmol) of a 1.5 M solution of KOH in water. The mixture is stirred at room temperature for 30 min, and the solvent is removed in vacuo. The residue is taken up in 1,2-dimethoxyethane, and an excess of $PCl_5$ (6 mmol) is added, giving bis(pentafluoroethyl)phosphinous acid chloride, $(C_2F_5)_2PCl$, identified as described above.

Example 3

Ethyl bis(pentafluoroethyl)phosphinite

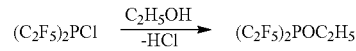

Bis(pentafluoroethyl)phosphinous acid chloride, $(C_2F_5)_2PCl$, obtainable in accordance with Example 2, is added to a mixture of ethanol and 4-dimethylaminopyridine in diethyl ether at room temperature. The precipitated product 4-dimethylaminopyridinium chloride is separated off, and the solution comprises ethyl bis(pentafluoroethyl)phosphinite, $(C_2F_5)_2POC_2H_5$.

The compound is isolated by conventional methods.
$^{19}$F NMR (diethyl ether; standard: $CCl_3F$), δ, ppm: −81.6 d, m ($2CF_3$), −122.6 m ($2CF_2$, A,B system), $^3J_{P,F}$=15 Hz.
$^{31}$P{$^{19}$F} NMR (diethyl ether; standard: 85% $H_3PO_4$), δ, ppm: 105.7 m, $^3J_{P,H}$=9 Hz.

Example 4

Tributylstannyl bis(pentafluoroethyl)phosphinite $(C_2F_5)_2POH+(C_4H_9)_3SnH \rightarrow (C_2F_5)_2POSn(C_4H_9)_3 + H_2$ 0.29 g (1.0 mmol) of bis(pentafluoroethyl)phosphinous acid $(C_2F_5)_2POH$, obtainable in accordance with Example 1, is condensed into a mixture of 0.22 g (0.8 mmol) of tributyltin hydride, $(n-C_4H_9)_3SnH$, in 10 ml of dry diethyl ether at −196° C. The reaction mixture is stirred at room temperature for 15 min, and the solvent is subsequently removed in vacuo. The residue is a colourless liquid, tributylstannyl bis(pentafluoroethyl)phosphinite. The compound is stable at room temperature under inert-gas conditions.

$^{19}$F NMR ($C_6D_6$; standard: $CCl_3F$), δ, ppm: −81.0 d, m ($2CF_3$), −124.3 d, d, m ($CF_2$, $F_A$), −124.9 d, d, m ($CF_2$, $F_B$), $^2J_{P,F(A)}$=74 Hz, $^2J_{P,F(B)}$=66 Hz, $^2J_{F(A),F(B)}$=319 Hz, $^3J_{P,F}$=14 Hz.
$^{31}${$^{19}$F} NMR ($C_6D_6$; standard: 85% $H_3PO_4$), δ, ppm: 107.4, $^2J_{P,Sn}$=48 Hz.
$^{119}$Sn NMR ($C_6D_6$; standard: $(CH_3)_4Sn$), δ, ppm: 180.7 d, $^2J_{Sn,P}$=48 Hz.

Example 5

Trimethylsilyl bis(pentafluoroethyl)phosphinite

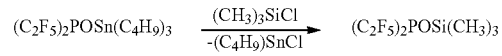

An excess of trimethylsilyl chloride, $(CH_3)_3SiCl$, is added to a mixture of tributylstannyl bis(pentafluoroethyl)phosphinite and tributyltin chloride, which is obtainable in accordance with the description of Example 1 or 4, giving trimethylsilyl bis(pentafluoroethyl)phosphinite, $(C_2F_5)_2POSi(CH_3)_3$.

The compound is isolated by conventional methods.

$^{19}$F NMR (diethyl ether; standard: CCl$_3$F), δ, ppm: −82.8 d (2CF$_3$), −124.1 d (2CF$_2$), $^2J_{P,F}$=73 Hz, $^3J_{P,F}$=15 Hz.

$^{31}$P NMR (diethyl ether; standard: 85% H$_3$PO$_4$), δ, ppm: 94.6 sept, quin; $^2J_{P,F}$=73 Hz, $^3J_{P,F}$=14 Hz.

$^{29}$Si{$^1$H} NMR (diethyl ether; standard: tetramethylsilane), δ, ppm: 31.1 d, $^2J_{Si,P}$=8 Hz.

Example 6

Bis(pentafluoroethyl)phosphine

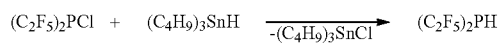

0.3 g (1.0 mmol) of bis(pentafluoroethyl)phosphinous acid chloride, (C$_2$F$_5$)$_2$PCl, obtainable in accordance with Example 2, is condensed into a degassed solution of 0.61 g (2.0 mmol) of tributyltin hydride, (n-C$_4$H$_9$)$_3$SnH, in 1,6-dibromohexane. The mixture is stirred at room temperature for one hour, and the volatile compounds are subsequently removed under dynamic vacuum conditions. Three cold traps are used: −30° C., −78° C. and −196° C. The cold trap at −196° C. contains a colourless liquid, bis(pentafluoroethyl)phosphine, (C$_2$F$_5$)$_2$PH. The compound is stable at room temperature under inert-gas conditions.

$^1$H NMR (C$_6$D$_6$; standard: TMS), δ, ppm: 3.7 d, m, $^1J_{P,H}$=232 Hz.

$^{19}$F NMR (C$_6$D$_6$; standard: CCl$_3$F), δ, ppm: −83.5 d, m (2CF$_3$), −102.3 d, m (CF$_2$, F$_A$), −108.9 d, m (CF$_2$, F$_B$), $^3J_{P,F}$=15 Hz.

$^{31}$P NMR (C$_6$D$_6$; standard: 85% H$_3$PO$_4$), δ, ppm: −51.6 d, m, $^1J_{P,H}$=230 Hz.

Example 7

Sodium bis(pentafluoroethyl)phosphinite

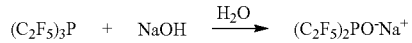

A solution of 1.16 g (3.0 mmol) of tris(pentafluoroethyl)phosphine, (C$_2$F$_5$)$_3$PH, in 1,2-dimethoxyethane is treated with an excess (6 mmol) of a 1.5 M solution of NaOH in water. The mixture is stirred at room temperature for 30 min, and the solvent is subsequently removed in vacuo, giving a colourless residue, sodium bis(pentafluoroethyl)phosphinite, (C$_2$F$_5$)$_2$PONa.

$^{19}$F NMR (dimethoxyethane; standard: CCl$_3$F), δ, ppm: −81.1 d (2CF$_3$), −126.3 d, d, m (CF$_2$, F$_A$), −127.4 d, d, m (CF$_2$, F$_B$), $^2J_{P,F(A)}$=67 Hz, $^2J_{P,F(B)}$=54 Hz, $^2J_{F(A),F(B)}$=314 Hz, $^3J_{P,F}$=12 Hz.

$^{31}$P NMR (dimethoxyethane; standard: 85% H$_3$PO$_4$), δ, ppm: 109.2 m.

Example 8

Bis(pentafluoroethyl)phosphinous acid

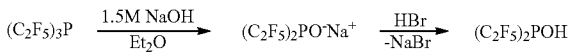

29 mmol of a 1.5 molar aqueous sodium hydroxide solution are added to a solution of 5.2 g (13.3 mmol) of tris(pentafluoroethyl)phosphine in 50 ml of diethyl ether, and the mixture is stirred at room temperature for 15 minutes. After removal of the aqueous phase, 50 ml of 1,6-dibromohexane are added, and all volatile constituents are removed overnight in vacuo. The reaction mixture is reacted with 13 mmol of HBr, and the product is separated off from the reaction mixture by means of fractional condensation (3 cold traps at −30° C., −78° C. and −196° C.). The compound is stable at room temperature under inert-gas conditions.

The product is characterised by means of NMR spectroscopy. The spectrum corresponds to the values indicated in Example 2.

Example 9

Chlorobis(pentafluoroethyl)phosphine

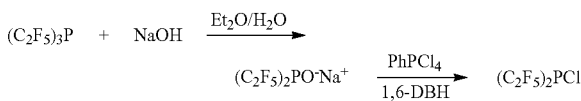

4.8 g (12.4 mmol) of tris(pentafluoroethyl)phosphine are condensed onto 50 ml of ether, and 25 mmol of 1.5 molar sodium hydroxide solution are added with stirring. After 30 minutes, 50 ml of 1,6-dibromohexane are added to the separated organic phase, and all volatile constituents are removed overnight in vacuo.

3.5 g (12.6 mmol) of PhPCl$_4$ are dissolved in 1,6-dibromohexane, degassed in vacuo and added dropwise to the phosphinite solution at 0° C. After the mixture has been stirred for 10 minutes, the product, chlorobis(pentafluoroethyl)phosphine, is separated off from the reaction mixture by means of fractional condensation (cold trap at −196° C.). The compound is stable at room temperature under inert-gas conditions.

The product is characterised by means of NMR spectroscopy. The spectrum corresponds to the values indicated in Example 1.

Example 10

4-Pentenyl bis(pentafluoroethyl)phosphinite

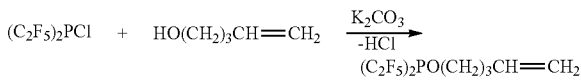

0.13 g (1.5 mmol) of 4-penten-1-ol is initially introduced in CH$_2$Cl$_2$ with 0.21 g (1.5 mmol) of K$_2$CO$_3$, and 0.46 g (1.5 mmol) of bis(pentafluoroethyl)phosphinous acid chloride, $(C_2F_5)_2PCl$, is condensed in. After the mixture has been stirred at room temperature for 20 minutes, the precipitate is filtered off. The product, 5-penten-1-yl bis(pentafluoroethyl) phosphinite, a colourless liquid, is isolated by fractional condensation and characterised by spectroscopy.

$^{19}F$ NMR (CDCl$_3$; standard: CCl$_3$F), δ, ppm: −81.8 d (2CF$_3$), −122.4 d (2CF$_2$,), $^2J_{P,F}$=74 Hz, $^3J_{P,F}$=13 Hz.

$^{31}P$ {$^{19}$} NMR (CDCl$_3$; standard: 85% H$_3$PO$_4$), δ, ppm: 105.6 t, $^3J_{P,H}$=8 Hz.

Example 11

9-Decenyl bis(pentafluoroethyl)phosphinite

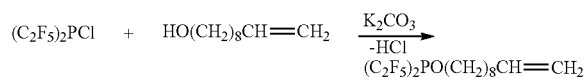

0.31 g (1.9 mmol) of 9-decen-1-ol is initially introduced in CH$_2$Cl$_2$ with excess K$_2$CO$_3$, and 0.64 g (2.1 mmol) of bis (pentafluoroethyl)phosphinous acid chloride, $(C_2F_5)_2PCl$, is condensed in. After the mixture has been stirred at room temperature for 30 minutes, the precipitate is filtered off, and volatile substances are removed in vacuo. The product, 9-decenyl bis(pentafluoroethyl)phosphinite, remains as a colourless, oily liquid, which is characterised by spectroscopy.

$^{19}F$ NMR (CDCl$_3$; standard: CCl$_3$F), δ, ppm: −81.9 d (2CF$_3$), −122.4 d (2CF$_2$,), $^2J_{P,F}$=74 Hz, $^3J_{P,F}$=13 Hz.

$^{31}P$ {$^{19}$} NMR (CDCl$_3$; standard: 85% H$_3$PO$_4$), δ, ppm: 105.5 m.

Example 12

Platinum complex with bis(pentafluoroethyl)phosphinous acid

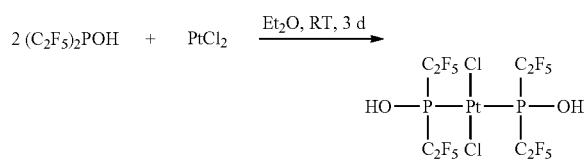

A mixture of 0.286 g (1 mmol) of bis(pentafluoroethyl) phosphinous acid, obtainable in accordance with Example 1, and 0.113 g (0.4 mmol) of platinum dichloride is stirred at room temperature for three days in 5 ml of dry diethyl ether. The mixture becomes yellow. After removal of diethyl ether, the platinum complex is isolated as a solid. The compound is stable at room temperature under inert-gas conditions.

$^{19}F$ NMR (diethyl ether; standard: CCl$_3$F), δ, ppm: −79.2 s (4CF$_3$),

−113.9 d, d, m (CF$_2$, F$_A$), −117.1 d, d, m (CF$_2$, F$_B$).

$^{31}P$ NMR (diethyl ether; standard: 85% H$_3$PO$_4$), δ, ppm: 81.4 m.

$^{195}Pt$ NMR (diethyl ether; standard: Na$_2$PtCl$_6$), δ, ppm: −3941 t, $^1J_{Pt,P}$=3313 Hz.

$^1H$ NMR (C$_6$D$_6$; standard: TMS), δ, ppm: 5.8 br.t.

Elemental analysis:
found 11.65% C, 0.23% H, calculated 11.46% C, 0.24% H.

Example 13

Palladium complex with bis(pentafluoroethyl)phosphinous acid

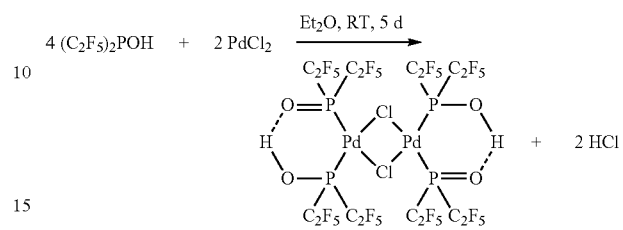

A mixture of 0.858 g (3 mmol) of bis(pentafluoroethyl) phosphinous acid, obtainable in accordance with Example 1, and 0.241 g (1.36 mmol) of palladium chloride is stirred at room temperature for five days in 25 ml of dry diethyl ether. The mixture becomes yellow. After removal of diethyl ether, the palladium complex is isolated as a solid.

$^{19}F$ NMR (diethyl ether; standard: CCl$_3$F), δ, ppm: −79.5 s (4CF$_3$), −110.5 d, d, m (CF$_2$, F$_A$), −116.2 d, d, m (CF$_2$, F$_B$).

$^{31}P$ NMR (diethyl ether; standard: 85% H$_3$PO$_4$), δ, ppm: 86.3 m.

Elemental Analysis:
found 13.82% C, 0.20% H, calculated 13.48% C, 0.20% H.

This palladium complex exists in solution in the presence of HCl in equilibrium with the corresponding mono-Pd complex I. However, removal of HCl and the solvent always gives the di-Pd complex.

Equilibrium Reaction:

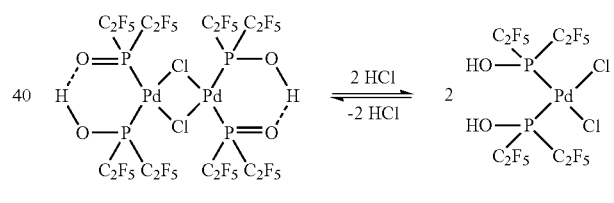

Example 14

Synthesis of Biphenyl Via Suzuki Coupling

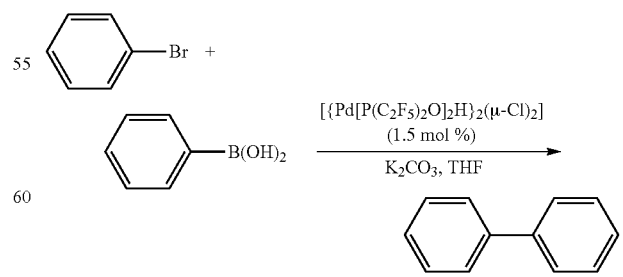

14a) 1.57 g (10 mmol) of bromobenzene and 4.15 g (30 mmol) of K$_2$CO$_3$ are added to a solution of 1.83 g (15 mmol) of phenylboronic acid in 20 ml of tetrahydrofuran. After the mixture has been stirred at room temperature for 15 minutes, 0.21 g (0.15 mmol) of [{Pd[P(C₂F₅)₂O]₂H}₂(μ-Cl)₂], prepared in accordance with Example 13, is added, and the reaction mixture is heated under reflux for 3 hours. After cooling and addition of 100 ml of water, the reaction mixture is extracted with 200 ml of hexane. The organic phase is washed with water and dried using MgSO₄. After filtration and removal of the solvent (in vacuo), 0.99 g of biphenyl is isolated as a white solid. The yield is 64%, based on the bromobenzene employed.

The product, biphenyl, is characterised by spectroscopy.

¹H NMR (CDCl₃; standard: TMS), δ, ppm: 7.35-7.65 m (10H).

¹³C {¹H} NMR (CDCl₃; standard: TMS), δ, ppm: 127.2; 127.3; 128.7; 141.3.

MS (20 eV): m/e (%): 154 (100), [M⁺].

14b) 1.57 g (10 mmol) of bromobenzene and 4.15 g (30 mmol) of K₂CO₃ are added to a solution of 1.83 g (15 mmol) of phenylboronic acid in 20 ml of tetrahydrofuran. After the mixture has been stirred at room temperature for 15 minutes, 0.21 g (0.15 mmol) of [{Pd[P(C₂F₅)₂O]₂H}₂(μ-Cl)₂], prepared in accordance with Example 13, is added, and the reaction mixture is heated under reflux for 18 hours. After cooling and addition of 100 ml of water, the reaction mixture is extracted with 200 ml of hexane. The organic phase is washed with water and dried using MgSO₄. After filtration and removal of the solvent (in vacuo), 1.29 g of biphenyl are isolated as a white solid. The yield is 84%, based on the bromobenzene employed.

The product, biphenyl, is characterised by spectroscopy.

The NMR spectrum corresponds to the values indicated in Example 14a).

14c)

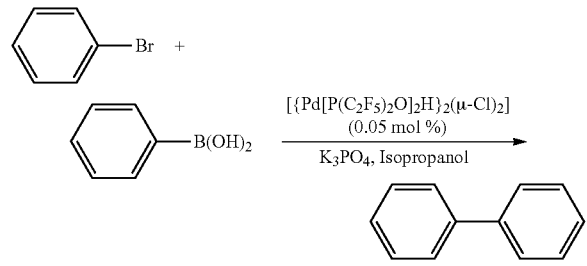

(28 mmol, 1 eq.) of bromobenzene and 9 g (42 mmol, 1.5 eq.) of K₃PO₄ are added to a solution of 5.13 g (42 mmol, 1.5 eq.) of phenylboronic acid in 60 ml of isopropanol. The mixture is stirred at room temperature for 45 minutes, and 0.02 g (14.03 μmol, 0.05 mol %) of [{Pd[P(C₂F₅)₂O]₂H}₂(μ-Cl)₂], prepared in accordance with Example 13, is subsequently added, and the reaction mixture is stirred at room temperature for 3 hours. After addition of 100 ml of water, the reaction mixture is extracted with 200 ml of hexane. The organic phase is washed with saturated sodium chloride solution and dried using MgSO₄. After filtration and removal of the solvent (in vacuo), 3.16 g of biphenyl are isolated as a white solid. The yield is 73%, based on the amount of bromobenzene employed.

The NMR spectrum corresponds to the values indicated in Example 14a).

Example 15

Synthesis of 2,4'-difluorobiphenyl via Suzuki Coupling

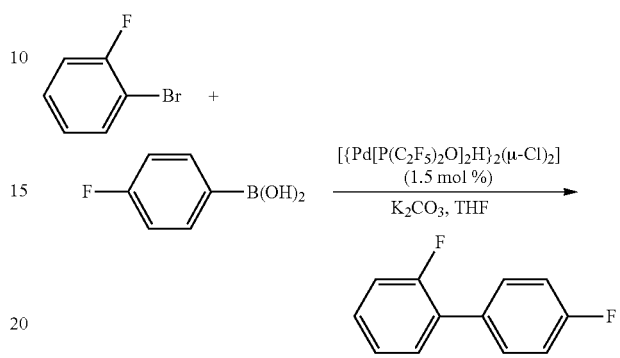

1.75 g (10 mmol) of 1-bromo-4-fluorobenzene and 4.15 g (30 mmol) of K₂CO₃ are added to a solution of 2.09 g (15 mmol) of 4-fluorophenylboronic acid in 20 ml of tetrahydrofuran. After the mixture has been stirred at room temperature for 15 minutes, 0.21 g (0.15 mmol) of [{Pd[P(C₂F₅)₂O]₂H}₂(μ-Cl)₂], prepared in accordance with Example 13, is added, and the reaction mixture is boiled for 18 hours. After cooling and addition of 100 ml of water, the reaction mixture is extracted with 200 ml of hexane. The organic phase is washed with water and dried using MgSO₄. After filtration and removal of the solvent (in vacuo), 1.35 g of 2,4'-difluorobiphenyl are isolated as a white solid. The yield is 70%, based on the 1-bromo-4-fluorobenzene employed. The product, 2,4'-difluorobiphenyl, is characterised by spectroscopy.

¹H NMR (MHz, CDCl₃; standard: TMS), δ, ppm: 7.20 m (1H), 7.37 m (1H), 7.25 m (1H), 7.45 m (1H), 7.57 m (2H), 7.18 m (2H).

¹⁹F NMR (282.4 MHz, CDCl₃; standard: CCl₃F), δ, ppm: −114.6 m (1F), −118.1 m (1F).

¹³C {¹H} NMR (75.47 MHz, CDCl₃; standard: TMS), δ, ppm: 162.5 d (1C), $^1J_{C,F}$=247 Hz; 159.7 d (1C), $^1J_{C,F}$=248 Hz; 131.8 d (1C), $^3J_{C,F}$=3.9 Hz; 130.8 d (1C), $^3J_{C,F}$=3.0 Hz; 130.6 d (2C), $^3J_{C,F}$=2.9 Hz; 129.1 d (1C), $3J_{C,F}$=8.2 Hz; 128.1 d (1C), $^2J_{C,F}$=13.4 Hz; 124.4 d (1C), $^4J_{C,F}$=3.7 Hz; 116.2 d (1C), $^2J_{C,F}$=22.6 Hz; 115.4 d (2C), $^2J_{C,F}$=21.5 Hz.

MS (20 eV): m/e (%): 190 (100), [M⁺].

Example 16

Synthesis of butyl (E)-3-(phenyl)acrylate; [(E)-butyl cinnamate] via Heck coupling

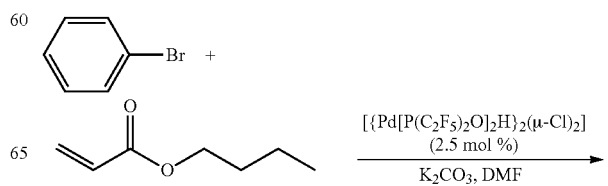

0.38 g (2.9 mmol) of butyl acrylate and 0.30 g (2.2 mmol) of $K_2CO_3$ are added to a solution of 0.32 g (2.0 mmol) of bromobenzene in 20 ml of dimethylformamide. After the mixture has been stirred at room temperature for 5 minutes, 0.08 g (0.05 mmol) of $[\{Pd[P(C_2F_5)_2O]_2H\}_2(\mu\text{-Cl})_2]$, prepared in accordance with Example 13, is added, and the reaction mixture is heated under reflux for 20 hours. After cooling and addition of 100 ml of water, the reaction mixture is extracted with 100 ml of diethyl ether. The organic phase is washed with water and dried using $MgSO_4$. After filtration and removal of the solvent (in vacuo), 0.26 g of butyl (E)-3-(phenyl)acrylate is isolated as a colourless oil. The yield is 64%, based on the bromobenzene employed.

The product, butyl (E)-3-(phenyl)acrylate, is characterised by spectroscopy.

$^1H$ NMR (CDCl$_3$; standard: TMS), δ, ppm: 7.70 d (1H, CH=), $^3J_{H,H}$=16 Hz; 7.55 m (2H, ArH); 7.40 m (3H, ArH); 6.46 d (1H, =CHCO$_2$Bu), $^3J_{H,H}$=16 Hz; 4.23 t (2H, CH$_2$), $^3J_{H,H}$=6,5 Hz; 1.71 m (2H, CH$_2$); 1.45 m (2H, CH$_2$); 0.98 t (3H, CH$_3$); $^3J_{H,H}$=7.5 Hz.

$^{13}C\{^1H\}$ NMR (CDCl$_3$; standard: TMS), δ, ppm: 167.0; 144.5; 134.4; 130.2; 128.8; 128.0; 118.2; 64.3; 30.7; 19.1; 13.7.

Example 17

Synthesis of butyl 2-fluoro-3-(phenyl)acrylate via Heck coupling 0.38 g (2.9 mmol, 1.5 eq.) of butyl acrylate and 0.3 g (2.2 mmol, 1.1 eq.) of $K_2CO_3$ are added to a solution of 0.36 g (2.0 mmol, 1.0 eq.) of 1-bromo-2-fluorobenzene in 20 ml of dimethylformamide. The mixture is stirred at room temperature for 5 minutes. 0.08 g (0.05 mmol) of $[\{Pd[P(C_2F_5)_2O]_2H\}_2(\mu\text{-Cl})_2]$, prepared in accordance with Example 13, is subsequently added, and the reaction mixture is heated under reflux for 20 hours, giving butyl 2-fluoro-3-(phenyl)acrylate.

$^{19}F$ NMR (282.4 MHz, CDCl$_3$; standard: CCl$_3$F), δ, ppm: −116.3 m.

$^1H$ NMR (300.13 MHz, CDCl$_3$; standard: TMS), δ, ppm: 7.77 d (1H, CH=), $^3J_{H,H}$=16 Hz; 7.48 t,d (1H, ArH), $^3J_{H,H}$=7.6 Hz, $^4J_{H,H}$=1.8 Hz; 7.29 m (1H, ArH); 7.06 m (2H); 6.49 d (1H, =CHCO$_2$Bu), $^3J_{H,H}$=16 Hz; 4.18 t (2H, CH$_2$), $^3J_{H,H}$=6.7 Hz; 1.65 m (2H, CH$_2$); 1.40 m (2H, CH$_2$); 0.92 t (3H, CH$_3$); $^3J_{H,H}$=7.2 Hz.

$^{13}C\{^1H\}$ NMR (75.47 MHz, CDCl$_3$; standard: TMS), δ, ppm: 166.7 s; 161.3 d ($^1J_{C,F}$=254 Hz); 137.0 s; 131.8 d ($^xJ_{C,F}$=8.7 Hz); 128.9 d ($^xJ_{C,F}$=2.9 Hz); 124.3 d ($^xJ_{C,F}$=3.6 Hz); 122.5 d ($^2J_{C,F}$=11.6 Hz); 120.8 d ($^4J_{C,F}$=6.5 Hz); 116.0 d ($^xJ_{C,F}$=21.9 Hz); 64.5 s; 30.8 s; 19.1 s; 13.6 s.

Example 18

Synthesis of 3-fluorobiphenyl via Suzuki coupling 12.27 g (70.2 mmol, 1 eq.) of 1-bromo-3-fluorobenzene and 44.7 g (210.5 mmol, 3 eq.) of $K_3PO_4$ are added to a solution of 12.83 g (105.3 mmol, 1.5 eq.) of phenylboronic acid in 200 ml of isopropanol. The mixture is stirred at room temperature for 4 hours. 0.0021 g (14.8 μmol, 0.0021 mol %) of $[\{Pd[P(C_2F_5)_2O]_2H\}_2(\mu\text{-Cl})_2]$, prepared in accordance with Example 13, is subsequently added, and the reaction mixture is stirred at room temperature for 20 hours, giving 3-fluorobiphenyl quantitatively.

Example 19

Synthesis of bis(pentafluoroethyl)thiophosphinous acid $(C_2F_5)_2PCl + Na_2S \xrightarrow{-NaCl} (C_2F_5)_2PS^-Na^+ \xrightarrow[-NaCl]{HBr} (C_2F_5)_2PSH$ 0.04 g (0.5 mmol) of Na$_2$S is initially introduced in dichloromethane, and 0.5 mmol of bis(pentafluoroethyl)phosphinous acid chloride, $(C_2F_5)_2PCl$, obtainable in accordance with Example 2, is condensed in. After the mixture has been stirred for 20 hours, volatile substances are removed in vacuo. A colourless precipitate remains, which is dissolved in diethyl ether, and 1,6-dibromohexane is added. Volatile constituents are removed in vacuo. Excess gaseous HBr is added to the reaction mixture, and the product is isolated by fractional condensation and characterised by spectroscopy.

$^{19}F$ NMR (solvent: C$_6$D$_6$; standard: CCl$_3$F), δ, ppm: −77.2 d (2CF$_3$), −112.4 d (2CF$_2$), $^2J_{P,F}$=61 Hz, $^3J_{P,F}$=15 Hz.

$^{31}P\{^{19}\}$ NMR (solvent: C$_6$D$_6$; standard: 85% H$_3$PO$_4$), δ, ppm: 17.4 d, $^2J_{P,H}$=25 Hz.

The invention claimed is:

1. A transition-metal complex containing at least one compound of the formula I

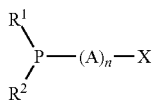

wherein
R¹ and R² are each, independently of one another, a straight-chain or branched perfluoroalkyl group having 2 to 12 C atoms,
A is O,
X stands for H, straight-chain or branched alkyl groups having 1 to 18 C atoms, cycloalkyl having 3 to 7 C atoms, alkenyl having 2 to 12 C atoms, alkynyl having 2 to 12 C atoms, aryl, alkyl-aryl, Si(R⁰)₃ or Sn(R⁰)₃,
R⁰ stands for a straight-chain or branched alkyl group having 1 to 8 C atoms, and
n stands for the integer 1,
in a complex with a transition metal.

2. A transition-metal complex according to claim 1, wherein M¹ and M² are, each independently, a transition metal selected from the group consisting of Pt, Pd, Rh, Ru and Ni.

3. A transition-metal complex according to claim 1, which is of the following formula

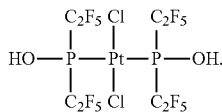

4. A transition-metal complex according to claim 1, which is of the following formula

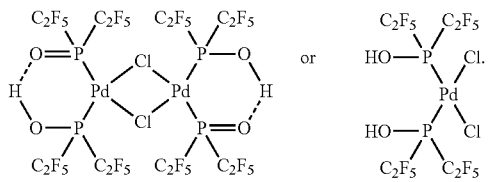

5. A transition-metal complex according to claim 1, wherein X stands for H.

6. A transition-metal complex according to claim 1, wherein X stands for a straight-chain or branched alkyl group having 1 to 4 C atoms, phenyl, benzyl, trimethylsilyl or tributylstannyl.

7. A transition-metal complex according to claim 1, wherein R¹ and R² are each, independently of one another, a straight-chain perfluoroalkyl group having 2 to 12 C atoms.

8. A transition-metal complex according to claim 1, wherein R¹ and R² are each, independently of one another, a branched perfluoroalkyl group having 3 to 12 C atoms.

9. A transition-metal complex according to claim 1, wherein R¹ and R² stand for pentafluoroethyl or linear nonafluorobutyl.

10. A transition-metal complex, which is of formula III, IV, V, VI or VII

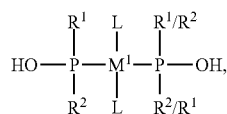

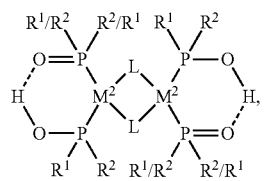

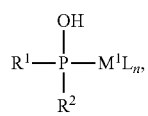

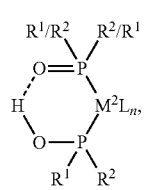

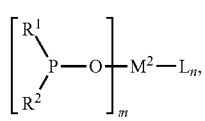

wherein
M¹ and M² are, each independently, a transition metal selected from the group consisting of Pt, Pd, Rh, Ir, Ru, Ni, Co, Fe, Au, Os, Ti, Zr, V, Cr, Mn, Mo, W, Re, Y, Nd, Yb, Sm, Tb or La,
L is an anionic, neutral or cationically charged ligand,
R¹ and R² are each, independently of one another, a straight-chain or branched perfluoroalkyl group having 2 to 12 C atoms, and
n denotes the number of ligands necessary to saturate the valences of M¹ or M²,
and wherein in formula VII, the sum n+m corresponds to the coordination number of the metal M².

11. A transition-metal complex according to claim 10, which is of formula III.

12. A transition-metal complex according to claim 10, which is of formula IV.

13. A transition-metal complex according to claim 10, which is of formula V.

14. A transition-metal complex according to claim 10, which is of formula VI.

15. A transition-metal complex according to claim 10, which is of formula VII.

16. A transition-metal complex according to claim 10, wherein R¹ and R² stand for pentafluoroethyl or linear nonafluorobutyl.

17. A process for preparing the transition-metal complex according to claim 10, which is of formula III, IV, V, VI or VII, comprising reacting at least one compound of formula I

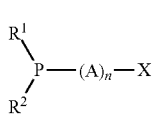

$$\text{I}$$

wherein
R¹ and R² are each, independently of one another, a straight-chain or branched perfluoroalkyl group having 2 to 12 C atoms,
A is O,
X stands for H, straight-chain or branched alkyl groups having 1 to 18 C atoms, cycloalkyl having 3 to 7 C atoms, alkenyl having 2 to 12 C atoms, alkynyl having 2 to 12 C atoms, aryl, alkyl-aryl, $Si(R^0)_3$ or $Sn(R^0)_3$,
R⁰ stands for a straight-chain or branched alkyl group having 1 to 8 C atoms, and
n stands for the integer 1,
with a precursor compound $M^1L_2$ or $M^2L_2$, wherein $M^1$, $M^2$ and L are defined as for the compounds of formulae III, IV, V, VI and VII.

* * * * *

UNITED STATES PATENT AND TRADEMARK OFFICE
CERTIFICATE OF CORRECTION

PATENT NO. : 8,648,202 B2  Page 1 of 1
APPLICATION NO. : 13/055561
DATED : February 11, 2014
INVENTOR(S) : Hoge et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 169 days.

Signed and Sealed this

Twenty-ninth Day of September, 2015

Michelle K. Lee
*Director of the United States Patent and Trademark Office*